US012037419B2

(12) United States Patent
Diamond

(10) Patent No.: US 12,037,419 B2
(45) Date of Patent: Jul. 16, 2024

(54) C1Q AND HMGB1 FUSION PROTEINS AND USES THEREOF

(71) Applicant: The Feinstein Institutes for Medical Research, Manhasset, NY (US)

(72) Inventor: Betty A. Diamond, Bronx, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 458 days.

(21) Appl. No.: 17/499,043

(22) Filed: Oct. 12, 2021

(65) Prior Publication Data

US 2022/0089644 A1  Mar. 24, 2022

Related U.S. Application Data

(60) Division of application No. 16/263,389, filed on Jan. 31, 2019, now Pat. No. 11,168,112, which is a continuation-in-part of application No. PCT/US2017/044307, filed on Jul. 28, 2017.

(60) Provisional application No. 62/370,402, filed on Aug. 3, 2016.

(51) Int. Cl.
| | |
|---|---|
| *C07K 7/08* | (2006.01) |
| *A61K 38/00* | (2006.01) |
| *A61P 37/06* | (2006.01) |
| *C07K 14/47* | (2006.01) |
| *C07K 16/28* | (2006.01) |
| *C07K 16/46* | (2006.01) |

(52) U.S. Cl.
CPC ............... *C07K 7/08* (2013.01); *A61P 37/06* (2018.01); *C07K 14/4702* (2013.01); *C07K 14/472* (2013.01); *C07K 16/2803* (2013.01); *C07K 16/46* (2013.01); *A61K 38/00* (2013.01); *C07K 2317/31* (2013.01); *C07K 2317/72* (2013.01); *C07K 2317/732* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 2008/0311122 A1 | 12/2008 | Wu et al. |
| 2010/0105874 A1 | 4/2010 | Schuurman et al. |
| 2015/0104472 A1 | 4/2015 | Diamond |
| 2016/0139120 A1 | 5/2016 | Barile et al. |

FOREIGN PATENT DOCUMENTS

| | | |
|---|---|---|
| WO | 2007054090 A1 | 5/2007 |
| WO | 200802543 A1 | 1/2008 |
| WO | 2013104901 A2 | 7/2013 |

OTHER PUBLICATIONS

Wang et al., "sRAGE Induces Human Monocyte Survival and Differentiation," J. Immunol., Aug. 1, 2010, vol. 185, No. 3, pp. 1822-1835.
Gong et al., "The Anti-Inflammatory Activity of HMGB1 a Box Is Enhanced When Fused With C-Terminal Acidic Tail," Journal of Biomedicine and Biotechnology, 2010, vol. 2010, Article ID 915234, 6 pages.
Moody et al., "Receptor Crosslinking: a General Method to Trigger Internalization and Lysosomal Targeting of Therapeutic Receptor:Ligand Complexes," Journal of the American Society of Gene and Cell Therapy, Dec. 2015 (advance online publication Oct. 27, 2015), vol. 23, No. 12, pp. 1888-1898.
Son et al., "C1q-Based Tolerance Mechanism in HMGB1-Mediated Activation of Human Monocytes (IRM5P.649)," The Journal of Immunology, May 1, 2015, vol. 194, Issue 1, Supplement 1, 59.14, 3 pages.
Bosch et al., "The DWEYS Peptide in Systemic Lupus Erythematosus," Trends in Molecular Medicine, Apr. 2012, vol. 18, No. 4, pp. 215-223.
BioLegend, "Alexa Fluor® 647 Anti-Human CD305 (LAIR1) Antibody," https://www.biolegend.com/en-us/products/alexa-fluor-647-anti-human-cd305-lair-1-antibody-5976, Version 2, Revision Date Jun. 27, 2014, 4 pages.
Brodeur et al., "Reduction of Advanced-Glycation End Products Levels and Inhibition of RAGE Signaling Decreases Rat Vascular Calcification Induced by Diabetes," PLoS ONE, Jan. 21, 2014, vol. 9, No. 1, e85922, 10 pages.
Chowdhury et al., "Identification of Crosslinked Peptides After Click-Based Enrichment Using Sequential CID and ETD Tandem Mass Spectrometry," Anal. Chem., Jul. 1, 2009, vol. 81, No. 13, pp. 5524-5532.
PCT International Search Report and Written Opinion dated Oct. 13, 2017 in connection with PCT International Application No. PCT/US2017/44307.
Chen et al., "Fusion Protein Linkers: Property, Design and Functionality," Adv. Drug Deliv. Rev., Oct. 15, 2013, vol. 65, No. 10, pp. 1357-1367.
Kong et al., "High-Mobility-Group Box Protein 1 a Box Reduces Development of Sodium Laurate-Induced Thromboangiitis Obliterans in Rats," Journal of Vascular Surgery, Jan. 2013, vol. 57, No. 1, pp. 194-204.
Extended European Search Report dated Dec. 9, 2019 from European Patent Application No. EP 17 83 7435.
Maldonado et al., "Rapamycin- and TGFbeta-Treated Dendritic Cells Induce Tolerance and de novo Differentiation of Regulatory T Cells in vitro and in vivo," Keystone Symposia—Abstract Book, Mar. 3, 2009, Poster Abstract 319 from Wednesday, Apr. 1: Poster Session 3 on p. 242, pp. 1-312.
López-Díez et al., "Cellular Mechanisms and Consequences of Glycation in Atherosclerosis and Obesity," Biochimica et Biophysica Acta, vol. 1862, 2016, pp. 2244-2252.
Thielens et al., "C1q: a Fresh Look Upon an Old Molecule," Molecular Immunology, vol. 89, 2017, pp. 73-83.
EPO Office Action dated Nov. 12, 2020 from European Patent Application No. 17837435.1.

*Primary Examiner* — Daniel C Gamett

(74) *Attorney, Agent, or Firm* — Amster, Rothstein & Ebenstein LLP

(57) ABSTRACT

Fusion proteins of C1q peptides and HMBG1 A-box or HMBG1 B-box, or C1q peptides and DWESY peptide are provided, and methods of use thereof.

7 Claims, 31 Drawing Sheets

Specification includes a Sequence Listing.

C1q A peptide:
KGEQGEPGAPGI

HMGB1 A-Box (22 aa):
MGKGDPKKPRGKMSSYAFFVQT

HMGB1 A-Box linker C1q:
MGKGDPKKPRGKMSSYAFFVQTGGGGSGGGGSGGGGSKGEQGEPGAPGI

HMGB1-B box linker C1q:
**KLKEKYEKDIAAYRAKGKPDAAKKGV

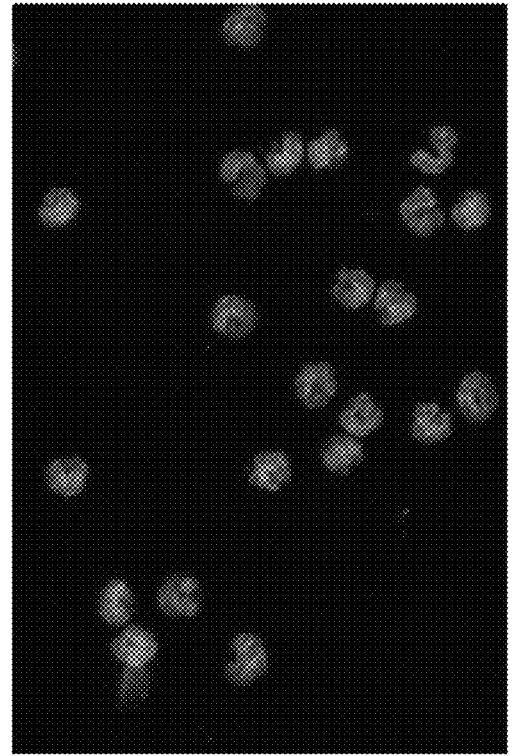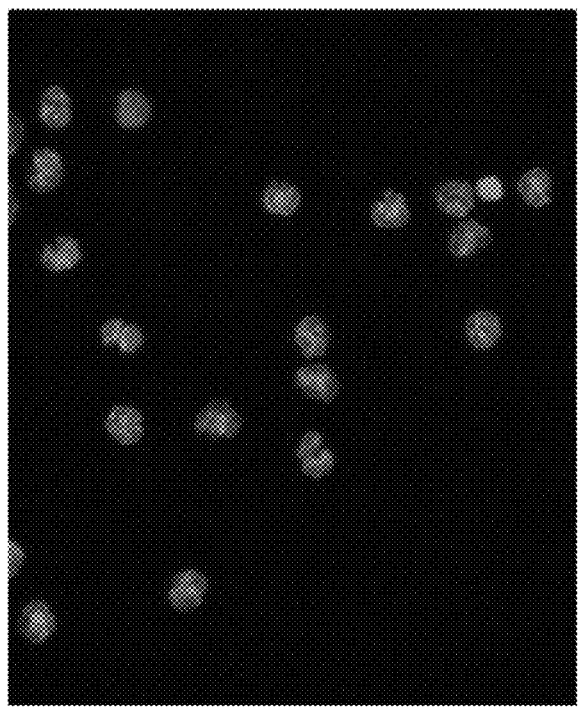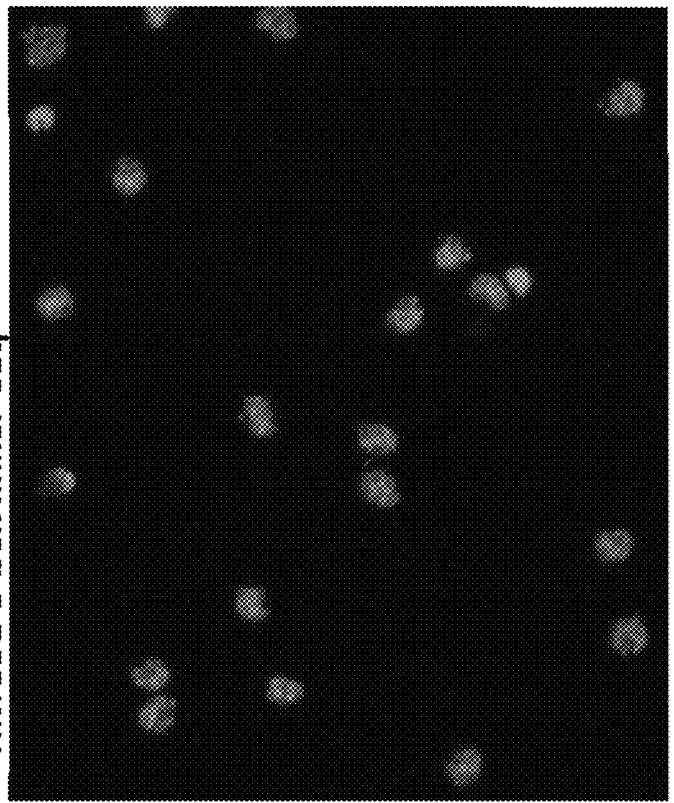
Fig. 14

200 micrograms/mouse (600mg/75Kg)

SEQUENCE LISTING

```
<160> NUMBER OF SEQ ID NOS: 11

<210> SEQ ID NO 1
<211> LENGTH: 22
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr
            20

<210> SEQ ID NO 2
<211> LENGTH: 34
<212> TYPE: PRT
<213> ORGANISM: Homo sapiens

<400> SEQUENCE: 2

Lys Leu Lys Glu Lys Tyr Glu Lys Asp Ile Ala Ala Tyr Arg Ala Lys
1               5                   10                  15

Gly Lys Pro Asp Ala Ala Lys Lys Gly Val Val Lys Ala Glu Lys Ser
            20                  25                  30

Lys Lys

<210> SEQ ID NO 3
```

```
<211> LENGTH: 12
<212> TYPE: PRT
<213> ORGANISM: Homo sapiens

<400> SEQUENCE: 3

Lys Gly Glu Gln Gly Glu Pro Gly Ala Pro Gly Ile
1               5                   10

<210> SEQ ID NO 4
<211> LENGTH: 245
<212> TYPE: PRT
<213> ORGANISM: Homo sapiens

<400> SEQUENCE: 4

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 5
<211> LENGTH: 9
<212> TYPE: PRT
<213> ORGANISM: Homo sapiens

<400> SEQUENCE: 5

Lys Gly Glu Gln Gly Glu Pro Gly Ala
1               5

<210> SEQ ID NO 6
<211> LENGTH: 21
```

```
<212> TYPE: PRT
<213> ORGANISM: Artificial Sequence
<220> FEATURE:
<223> OTHER INFORMATION: Artificial based on human

<400> SEQUENCE: 6

Lys Gly Glu Gln Gly Glu Pro Gly Ala Lys Gly Glu Gln Gly Glu Pro
1               5                   10                  15

Gly Ala Pro Gly Ile
            20

<210> SEQ ID NO 7
<211> LENGTH: 61
<212> TYPE: PRT
<213> ORGANISM: Artificial Sequence
<220> FEATURE:
<223> OTHER INFORMATION: Artificial based on human

<400> SEQUENCE: 7

Lys Leu Lys Glu Lys Tyr Glu Lys Asp Ile Ala Ala Tyr Arg Ala Lys
1               5                   10                  15

Gly Lys Pro Asp Ala Ala Lys Lys Gly Val Val Lys Ala Glu Lys Ser
                20                  25                  30

Lys Lys Gly Gly Gly Gly Ser Gly Gly Gly Ser Gly Gly Gly Gly
            35                  40                  45

Ser Lys Gly Glu Gln Gly Glu Pro Gly Ala Pro Gly Ile
    50                  55                  60

<210> SEQ ID NO 8
<211> LENGTH: 5
<212> TYPE: PRT
<213> ORGANISM: Homo sapiens

<400> SEQUENCE: 8

Asp Trp Glu Tyr Ser
1               5

<210> SEQ ID NO 9
<211> LENGTH: 21
<212> TYPE: DNA
<213> ORGANISM: Homo sapiens

<400> SEQUENCE: 9
cagcatccag aaggttcgtt a                                          21

<210> SEQ ID NO 10
<211> LENGTH: 49
<212> TYPE: PRT
<213> ORGANISM: Artificial Sequence
<220> FEATURE:
<223> OTHER INFORMATION: Artificial based on human

<400> SEQUENCE: 10

Met Gly Lys Gly Asp Pro Lys Lys Pro Arg Gly Lys Met Ser Ser Tyr
1               5                   10                  15

Ala Phe Phe Val Gln Thr Gly Gly Gly Ser Gly Gly Gly Gly Ser
                20                  25                  30

Gly Gly Gly Gly Ser Lys Gly Glu Gln Gly Glu Pro Gly Ala Pro Gly
            35                  40                  45

Ile

<210> SEQ ID NO 11
```

```
<211> LENGTH: 32
<212> TYPE: PRT
<213> ORGANISM: Artificial Sequence
<220> FEATURE:
<223> OTHER INFORMATION: Artificial based on human

<400> SEQUENCE: 11

Asp Trp Glu Tyr Ser Gly Gly Gly Gly Ser Gly Gly Gly Gly Ser Gly
1               5                   10                  15

Gly Gly Gly Ser Lys Gly Glu Gln Gly Glu Pro Gly Ala Pro Gly Ile
            20                  25                  30
```

C1Q AND HMGB1 FUSION PROTEINS AND USES THEREOF

CROSS-REFERENCE TO RELATED APPLICATIONS

This application is a divisional of U.S. patent application Ser. No. 16/263,389, filed Jan. 31, 2019, which is a continuation-in-part of and claims benefit of PCT International Application PCT/US2017/044307, filed Jul. 28, 2017, which claims priority to U.S. Provisional Application No. 62/370,402, filed Aug. 3, 2016, the contents of each of which are hereby incorporated by reference.

STATEMENT OF GOVERNMENT SUPPORT

This invention was made with government support under grant numbers AR065506, AR057084, and OD012042 awarded by the National Institutes of Health. The government has certain rights in the invention.

BACKGROUND OF THE INVENTION

Throughout this application various publications are referred to, including by number. Full citations for these references may be found at the end of the specification. The disclosures of these publications, and all patents, patent application publications and books referred to herein, are hereby incorporated by reference in their entirety into the subject application to more fully describe the art to which the subject invention pertains.

The ability of the mammalian immune system to avoid reactivity to self relies on a fine balance of multiple, inter-related, signaling pathways, in which excitatory pathways are balanced by inhibitory pathways. Systemic Lupus Erythematosus (SLE) is a disease in which the inhibitory pathways are inadequate and autoreactivity and inflammation result (1). In particular, SLE is characterized by activation of cytosolic toll-like receptors (TLRs) leading to an immunogenic and inflammatory milieu (2). To date, therapeutic strategies for SLE have been largely palliative or rely on non-specific immunosuppressive drugs with serious toxicities. Developing a targeted therapeutic requires a better understanding of the molecular mechanisms through which the body achieves a natural program of quiescence and how this immune homeostasis is disrupted in SLE.

The present invention addresses this need for new therapeutics to treat SLE and other immune and inflammatory disorders.

SUMMARY OF THE INVENTION

A polypeptide is provided comprising (i) a C1q dodecamer peptide, or a C1q nonamer peptide wherein the nonamer peptide comprises KGEQGEPGA (SEQ ID NO:5), and (ii) a HMBG1 A-box peptide or a HMBG1 B-box peptide.

Also provided is a method of treating an autoimmune inflammatory condition comprising administering an amount of a polypeptide as described herein effective to treat an autoimmune inflammatory condition.

Also provided is a method to quiesce a monocyte in a subject comprising administering an amount of the polypeptide as described herein effective to quiesce a monocyte in a subject.

Also provided is a method to induce an M2 phenotype in a monocyte in a subject and/or reducing an adaptive immune activation in a subject comprising administering an amount of the polypeptide as described herein effective to induce M2 phenotype in a monocyte in a subject and/or reducing an adaptive immune activation in a subject.

Also provided is a method of reducing a hyper-activated innate immune response in a subject comprising administering an amount of the polypeptide as described herein effective to treat reduce a hyper-activated innate immune response.

Also provided is a polypeptide comprising (i) a C1q dodecamer peptide, or a C1q nonamer peptide wherein the nonamer peptide is KGEQGEPGA (SEQ ID NO:5), and (ii) a DWEYS peptide.

Also provided is a method of treating an autoimmune inflammatory condition comprising administering an amount of the polypeptide as described herein comprising the DWEYS peptide effective to treat an autoimmune inflammatory condition.

Also provided is a method of treating an inflammatory condition in sepsis comprising administering an amount of the polypeptide as described herein comprising the DWEYS peptide effective to treat an inflammatory condition in sepsis.

Also provided is a method of maintaining a systemic lupus erythematosus (SLE) remission state in a subject having had SLE but in remission, comprising administering an amount of the polypeptide as described herein comprising the DWEYS peptide effective to maintain a remission state in a subject having had systemic lupus erythematosus.

Also provided is a method of reducing a hyper-activated innate immune response in a subject comprising administering an amount of the polypeptide as described herein comprising the DWEYS peptide effective to treat reduce a hyper-activated innate immune response.

A method is provided of cross-linking LAIR-1 and RAGE in a subject comprising contacting the LAIR-1 and RAGE with a composition administered to the subject that binds to LAIR-1 and RAGE comprising a polypeptide.

*P<0.05; P<0.01; *P<0.001. Data are representative of four independent experiments.

Figures 2A, 2B, 2C:
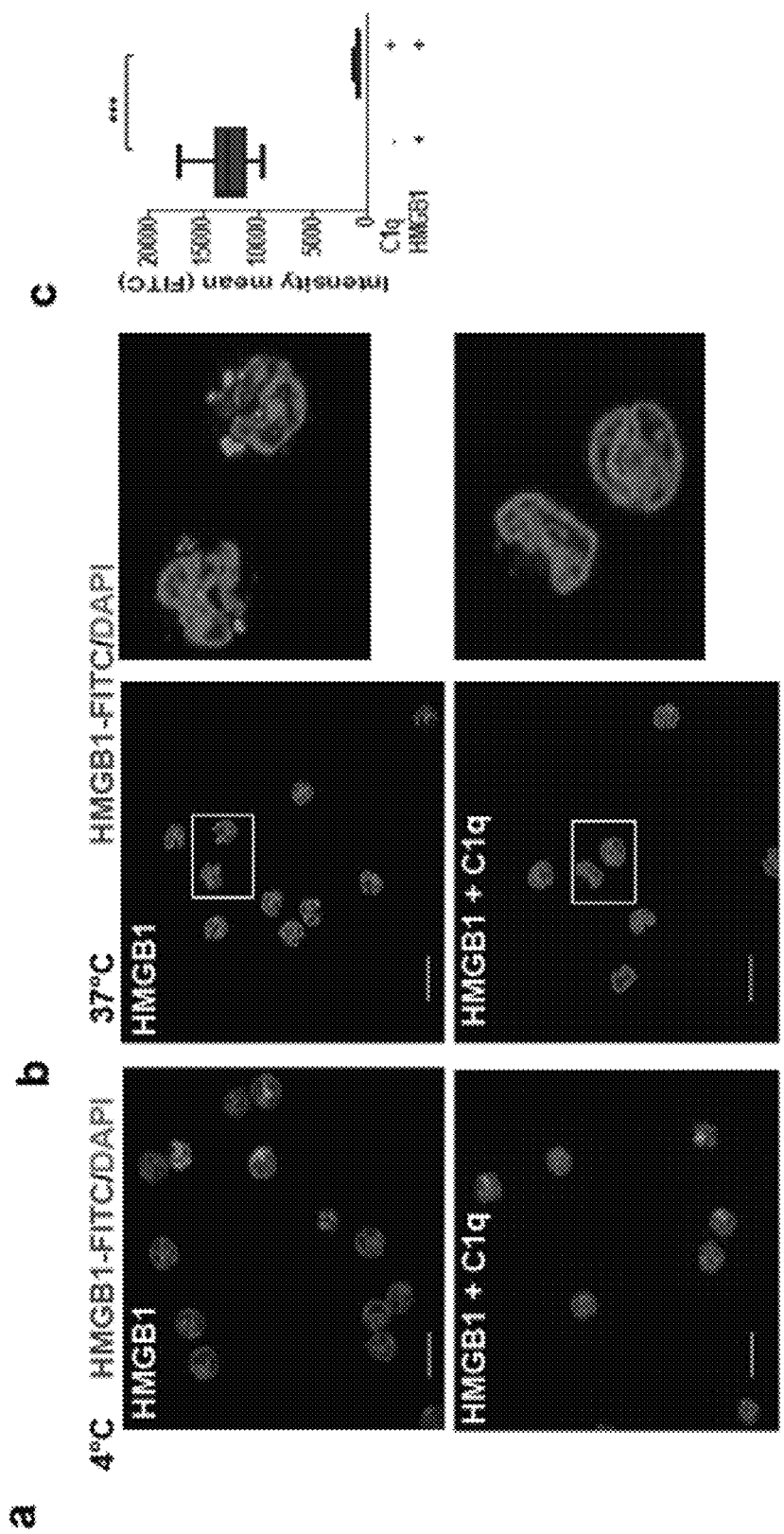

FIG. 2A-FIG. 2C. C1q inhibits HMGB1 internalization by human monocytes. Human monocytes were treated with FITC-conjugated HMGB1 (3 µg/ml) in the absence or presence of C1q (25 µg ml-1) for 15 min at 4° C. (2A) or 37° C. (2B). FITC-conjugated HMGB1 (green) and DAPI (blue) were viewed using Axiovert 200M digital deconvolution microscope (63×; oil). Scale bar: 10 µm. (2C) Mean intensity per cell was calculated over 200 cells by Zen2 software. Similar results were obtained in four independent experiments, and representative images are shown.

FIG. 3A-FIG. 3I. C1q, HMGB1 and soluble RAGE form a tri-molecular complex. (3A) C1q inhibits HMGB1-mediated IL-12a and MX1 transcription in wild type but not RAGE-deficient monocytes. mRNA expression in splenic monocytes of C57BL/6 wild type or RAGE deficient mice treated with HMGB1 (3 µg/ml) and co-incubated with or without C1q (25 µg/ml) for 6 h. R.E; relative expression (mean±s.d. of triplicates) not significant, ns; *P<0.05; **P<0.01. Data are representative of four independent experiments. (3B) Surface plasmon resonance (SPR) assay of C1q and RAGE binding; KD=855 nM. (3C) SPR assay of RAGE-C1q-HMGB1 trimolecular complex. sRAGE was immobilized onto a CMS chip and the first analyte (C1q, 200 nM) was added to saturation. HMGB1 (500 nM) was injected to the sRAGE-C1q complex in multiple pulses (left). HMGB1 was injected to immobilized sRAGE until the chip was saturated followed by C1q addition (right). (3D) SPR assay for HMGB1 and C1q binding; KD=200 nM. (3E) SPR assay of different redox states of HMGB1 and C1q binding. SPR experiments were repeated at three times; representative data are shown. (3F, 3G, 3H) C1q-coated beads were incubated with saturating amounts of HMGB1, followed by 250 ng or 500 ng of RAGE. (3I) Complexes were analyzed by Western blot using anti-RAGE, anti-Cbp antibody for HMGB1 or IR-labeled streptavidin for biotinylated-C1q. Experiments were repeated three times, representative data are shown.

Figures 4A, 4B:
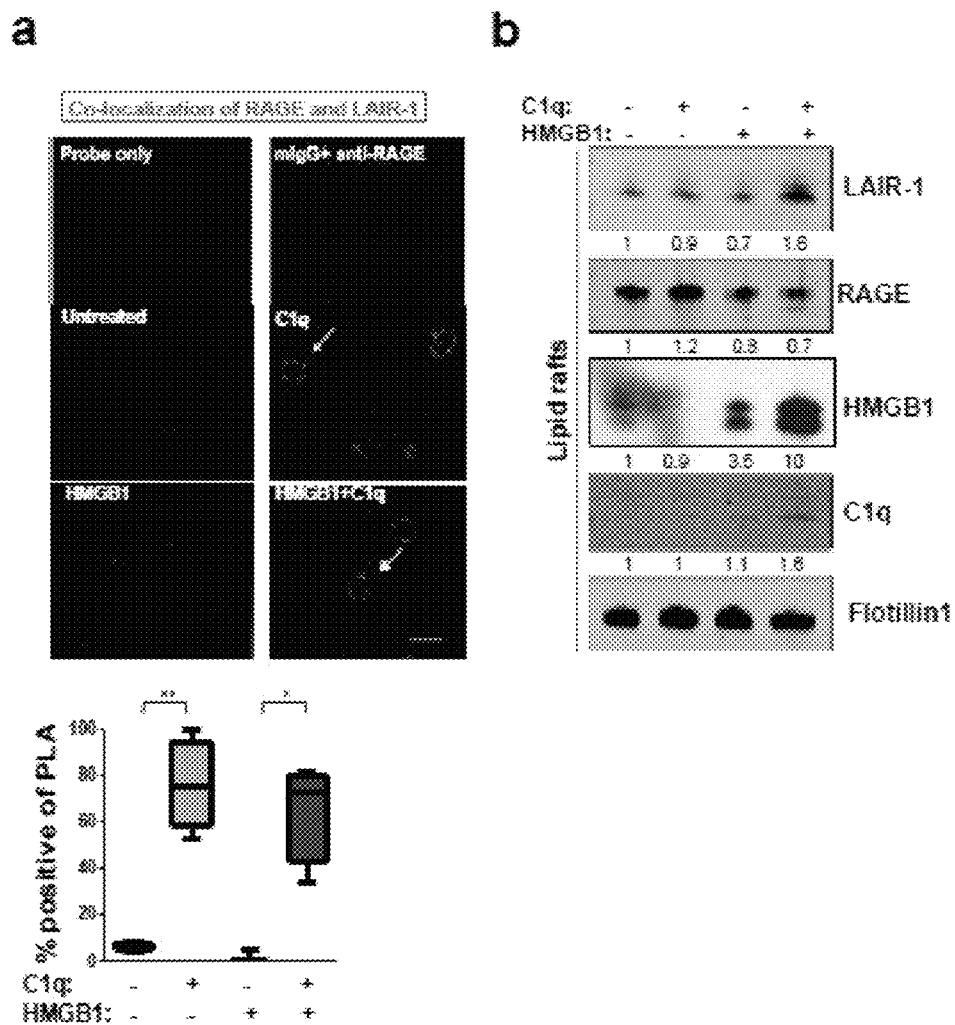

FIG. 4A-FIG. 4B. C1q and HMGB1 cross-link LAIR-1 and RAGE in lipid rafts. (4A) Colocalization of LAIR-1 and RAGE on the plasma membrane was assessed by proximity ligation assay (PLA). Red dots (PLA positive), representing colocalization between RAGE and LAIR-1, are only seen in the presence of C1q, with or without HMGB1. Percent PLA positive cells over total cells were counted from different random field (>200 cells). One of four similar assays is shown. (4B) Lipid raft fractions were concentrated and analyzed by Western blot for LAIR-1, RAGE, HMGB1, C1q or Flotillin1 as a lipid raft marker. Data are representative of three independent experiments.

FIG. 5A-FIG. 5E. C1q dephosphorylates RAGE, recruits SHP-1 to LAIR-1 and inhibits the HMGB1-induced NF-κB signaling pathway. (5A) Human monocytes were treated with C1q and/or HMGB1 and subjected to immunoprecipitation (IP) with antibodies to RAGE followed by immunoblotting with antibodies specific for phospho-serine (top) or RAGE (bottom). Numbers below the immunoblots indicate the signal intensity ratio. Data are representative of three independent experiments. (5B) Total cell lysates were subjected to immunophosphorylation array (R&D) to observe the phosphorylation of LAIR-1 ITIM motifs. Relative quantification for the phosphorylation of LAIR-1 was normalized to control spots. Data are representative of three independent experiments. (5C) Human monocytes were treated with C1q and/or HMGB1 and subjected to immunoprecipitation with antibodies to LAIR-1 followed by immunoblotting with antibodies for SHP-1 (top) or LAIR-1 (bottom). Data are representative of four independent experiments. (5D) Human monocytes were treated with C1q and/or HMGB1 and subjected to immunoblotting with antibodies for activated IKKα (P-IKKα, top), p65 (P-p65, middle) or β-actin. Experiments were repeated four times and representative data are shown. (5E) Nuclear translocation of NF-κB p65 was analyzed following HMGB1 or HMGB1 plus C1q stimulation for 1 h. Maximal fluorescent intensity was evaluated for DAPI (blue) and NF-κB p65 (red) across the red arrow. The percentage of maximal fluorescent intensity along the red arrow traced in the merged image is displayed. Scale bar: 10 µm. Data are representative of three independent experiments.

FIG. 6A-FIG. 6E. HMGB1 and C1q induce anti-inflammatory molecules and promote an M2-like phenotype. (a-e) Human monocytes treated with C1q (25 µg/ml) or C1q tail (53 µg/ml) and/or HMGB1 (3 µg/ml) for 24 h were processed for mRNA and protein. (6A) Mer tyrosine kinase as assessed by q-PCR (reft) and flow cytometry (right). R.E; relative expression. Error bars indicate mean±s.d. (6B) Programmed Death-Ligand 1 (PDL-1) was measured by q-PCR (left) and flow cytometry (right). (6C) IL-10 was measured by q-PCR (left) and ELISA of culture supernatant (right). (6D) CD163 as assessed by q-PCR (left) was determined by flow cytometry (right). (6E) In the presence of different concentration of C1q (10, 25, 50 or 75 µg/ml), Mer, PDL-1, IL-10 and CD163 mRNA transcription was assessed after 24 h stimulation. Statistical analysis was performed by One-way ANOVA and t-test; ns, not significant; * P<0.05,  P<0.01 * P<0.001. All data are representative of four independent experiments.

Figures 7A, 7B, 7C:
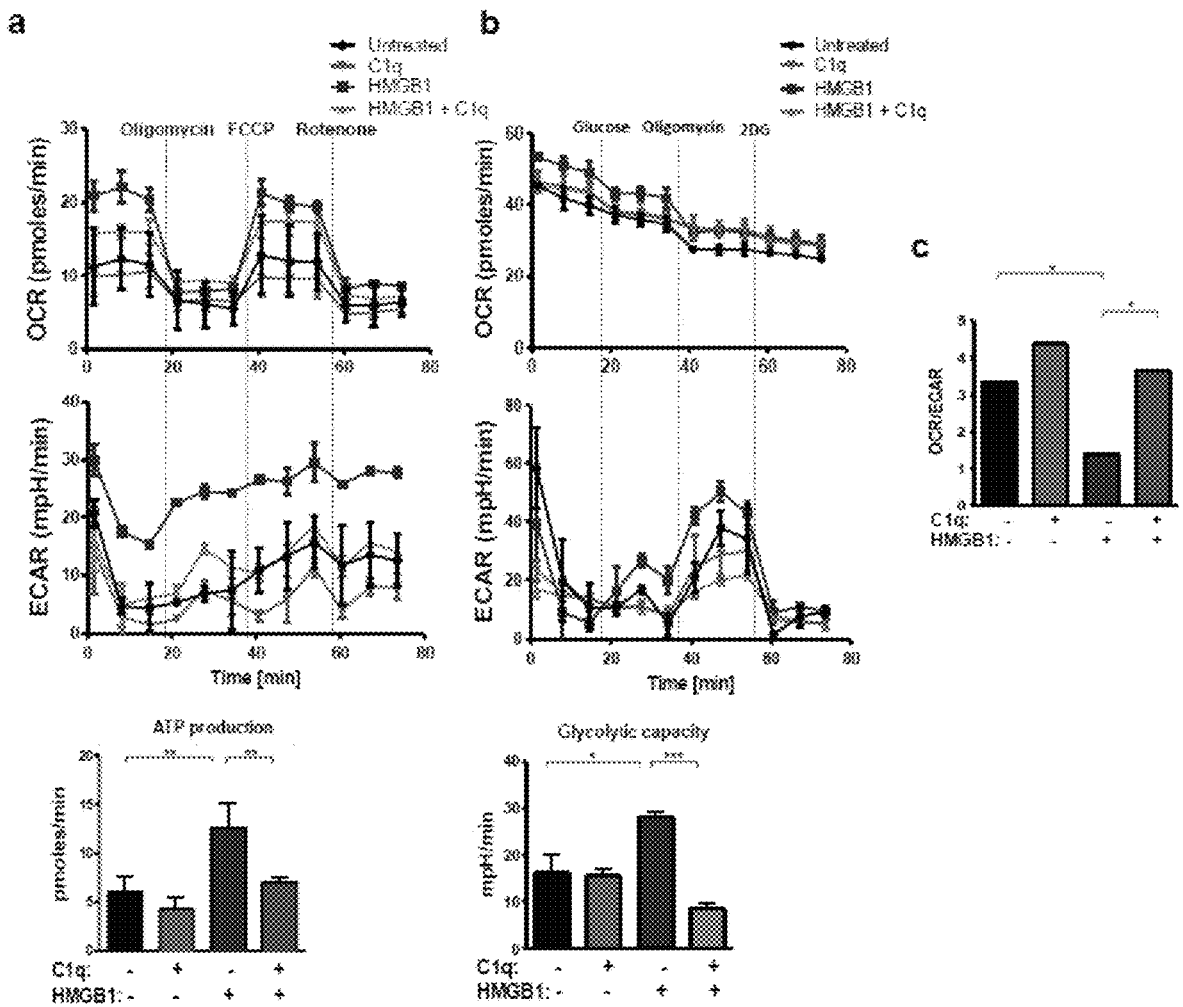

FIG. 7A-FIG. 7C. HMGB1 alters cellular metabolism, induces aerobic glycolysis, and is inhibited by C1q. HMGB1's effect on cellular mitochondrial (7A) and glycolytic (7B) activity was evaluated using a SeaHorse metabolic analyzer. Monocytes were treated with HMGB1 and/or C1q for 24 h, assessed for basal oxygen consumption rate (OCR) and extracellular acidification rate (ECAR), and then sequentially treated with listed reagents. One representative experiment of three is shown. (a) For evaluation of mitochondrial activity, cells were incubated with oligomycin, FCCP, and rotenone plus antimycin A. Mitochondrial ATP production was calculated by subtracting oxygen consumption following oligomycin treatment from basal levels. (b) For evaluation of cellular glycolytic activity, cells were incubated in assay media lacking glucose or pyruvate, then treated sequentially with glucose, oligomycin, and 2-deoxyglucose. Max glycolytic capacity following oligomycin treatment is shown. Statistical analysis was performed using One-way ANOVA with correction for multiple comparisons. * P<0.05, P<0.01 *P<0.001. (7C) HMGB1 treated cells showed a marked increase of glycolysis in comparison to oxidative phosphorylation (OCR/ECAR). Data represents sum of four independent experiments. Statistical analysis was performed by Kruskal-Wallis test/Dunn correction for subgroup analysis. *P<0.05.

Figures 8A, 8B:
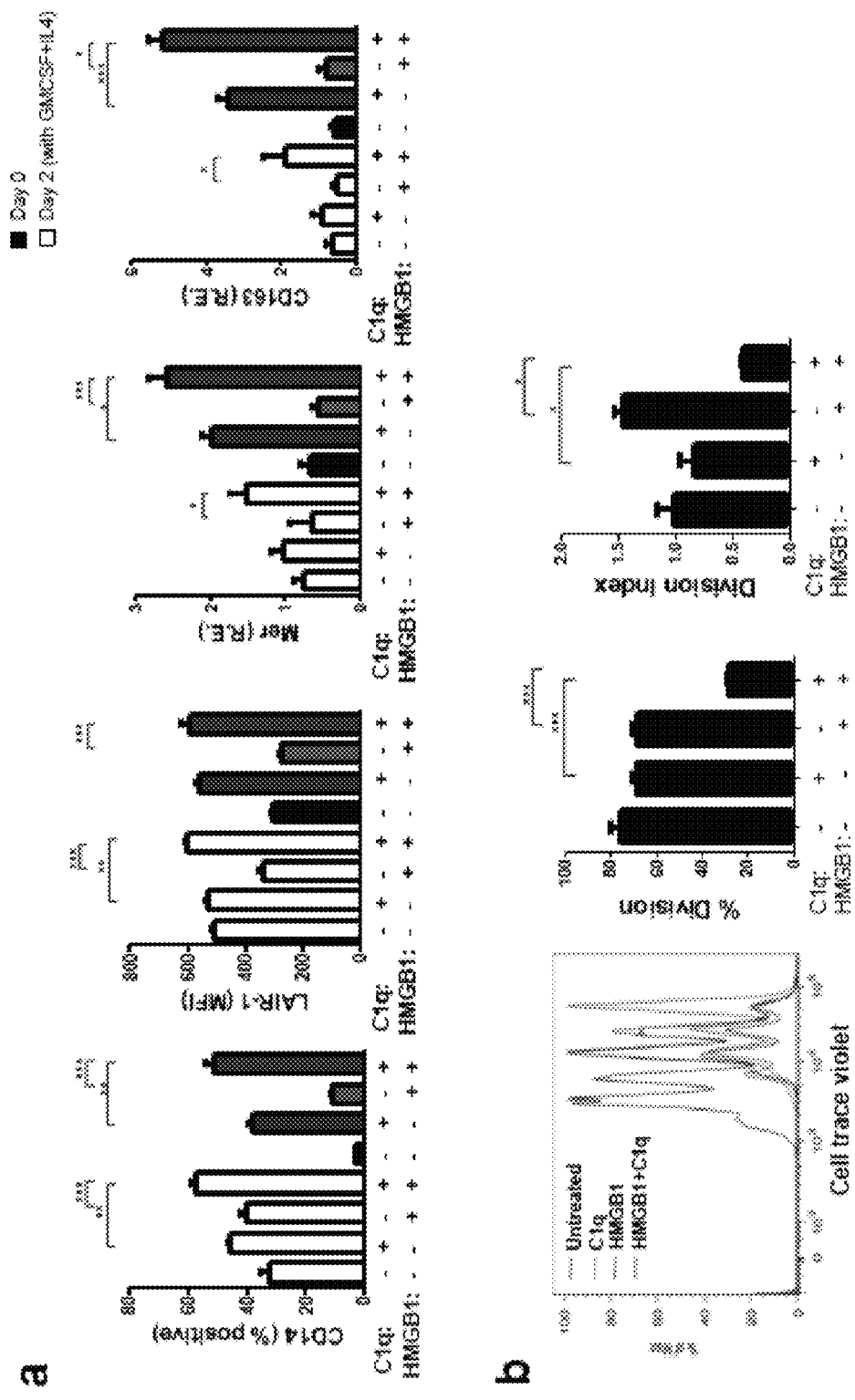

FIG. 8A-FIG. 8B. HMGB1 and C1q terminate M2-like macrophage phenotypes. Phenotype analysis of DC differentiation induced by GM-CSF and IL-4 was performed by flow cytometry. Monocytes were treated with C1q and/or HMGB1 for 24 h (Day 0), then further cultured with GM-CSF and IL-4 for 2 days (Day 2). (8A) High levels of CD14 and LAIR-1 represent suppression of DC differentiation. Data are expressed as mean±s.e.m. of triplicate samples. Transcription of Mer and CD163 were measured by q-PCR. Data are expressed as mean±s.d. of triplicate samples. Significant differences are indicated *P<0.05; P<0.01; *P<0.001 (t-test). Data are representative of three independent experiments. (8B) Monocytes were exposed to HMGB1 (3 µg/ml), C1q (25 µg/ml) or both for 24 h washed, and further incubated 2 days in X-Vivo 15 medium. Cell Trace Violet-stained allogeneic primary human CD4 T cells were added (2:1). After 4 days, the nonadherent cells were removed and assessed by flow cytometry. Live CD4+ T cells were analyzed. Significant differences are indicated *P<0.05; P<0.01; *P<0.001 (t-test). Data are representative of three independent experiments.

Figures 9A, 9B, 9C:
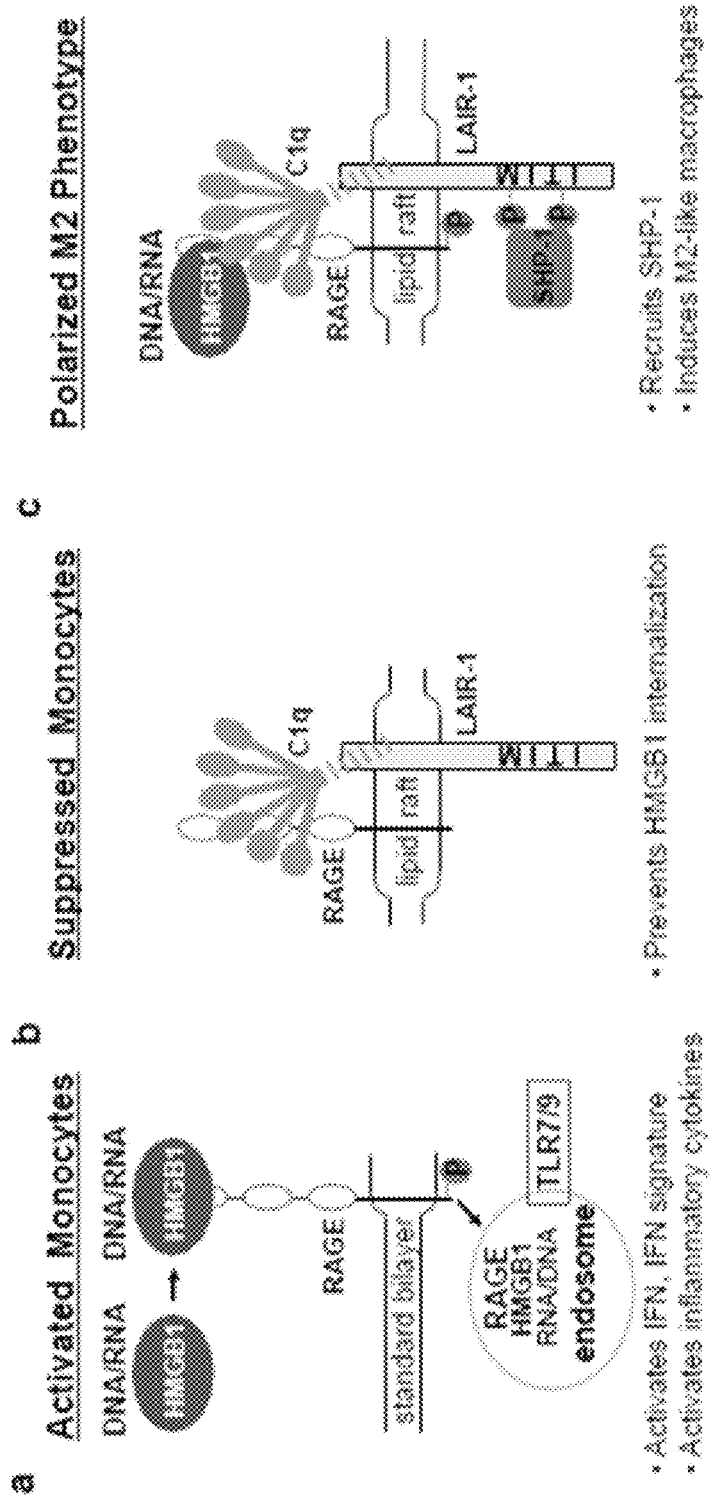

FIG. 9A-FIG. 9C. Model showing how C1q utilizes a natural pathway to dampen inflammation. (9A) DNA/RNA binding HMGB1 is internalized and activates endosomal TLRs and induces M1-like macrophages. (9B) In the presence of C1q without inflammation, C1q and LAIR-1 signaling prevents HMGB1 internalization. (9C) However, in inflammation, C1q mediates M2 differentiation by cross-linking RAGE and LAIR-1 in lipid rafts to facilitate. SHP-1 binding to LAIR-1 via phosphorylated ITIMs, and induces differentiation of M2-like macrophage.

Figure 10:
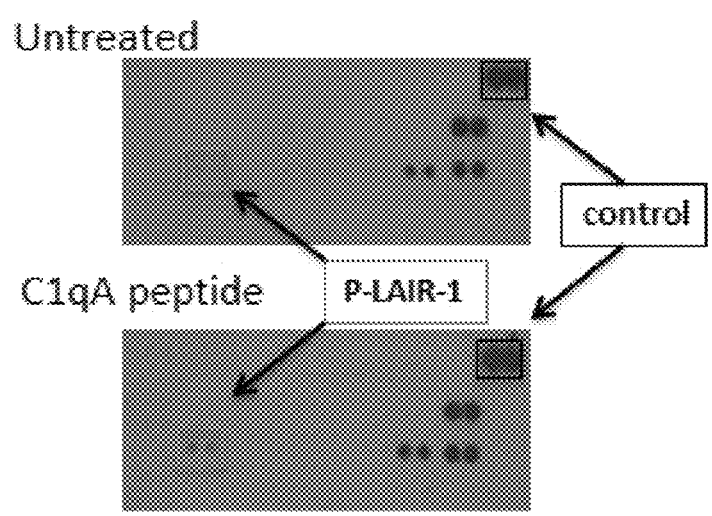

FIG. 10: Synthetic C1q peptide activates LAIR-1.

Figure 11:
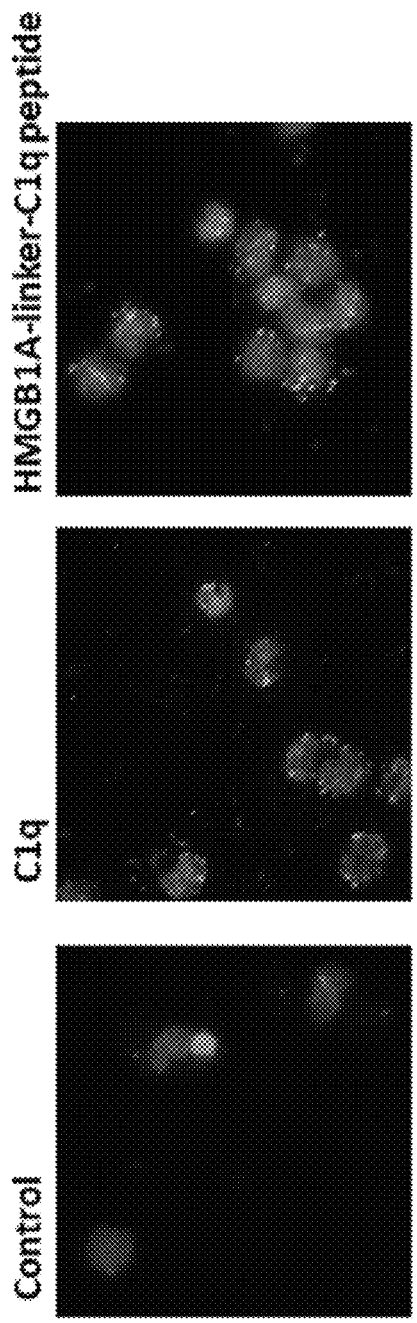

FIG. 11: HMGB1-linker-C1q peptide mimics C1q; cross-links RAGE and LAIR-1.

FIG. 12: Exemplary sequences of C1q A peptide (SEQ ID NO:3); HMGB1 A-Box (22 aa) (SEQ ID NO:1); HMGB1 A-Box linker C1q (SEQ ID NO:10); HMGB1-B box linker C1q (SEQ ID NO:7); and DWEYS linker C1q (SEQ ID NO:11).

Figure 13A:
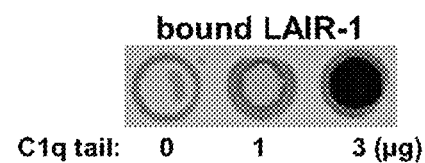
Figure 13B:
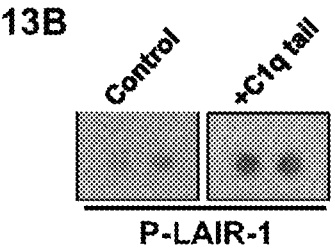

FIG. 13A-FIG. 13B: (13A)—Determination of bound LAIR-1 to C1q tail; (13B)—Determination of bound P-LAIR-1 to C1q tail.

FIG. 14: 15 min PLA for RAGE and LAIR-1—showing HMGB1-B box linker C1q, DWEYS linker C1q, and control.

Figure 15:
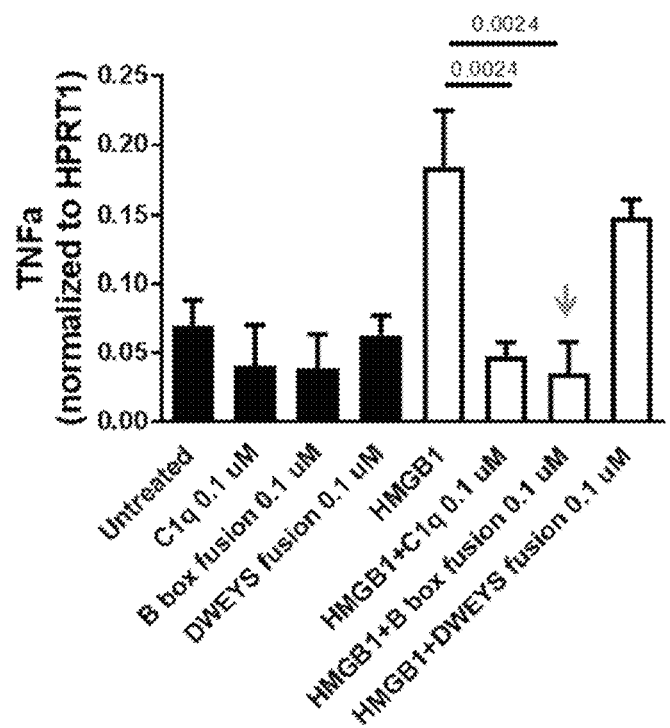

FIG. 15: B box fusion: HMGB1-B box linker C1q DWEYS fusion: DWEYS linker C1q. Left panel shows IL-6 levels after 4 hrs with each of the listed treatments. Right panel shows TNF-alpha levels after 4 hrs with each of the listed treatments.

Figure 16:
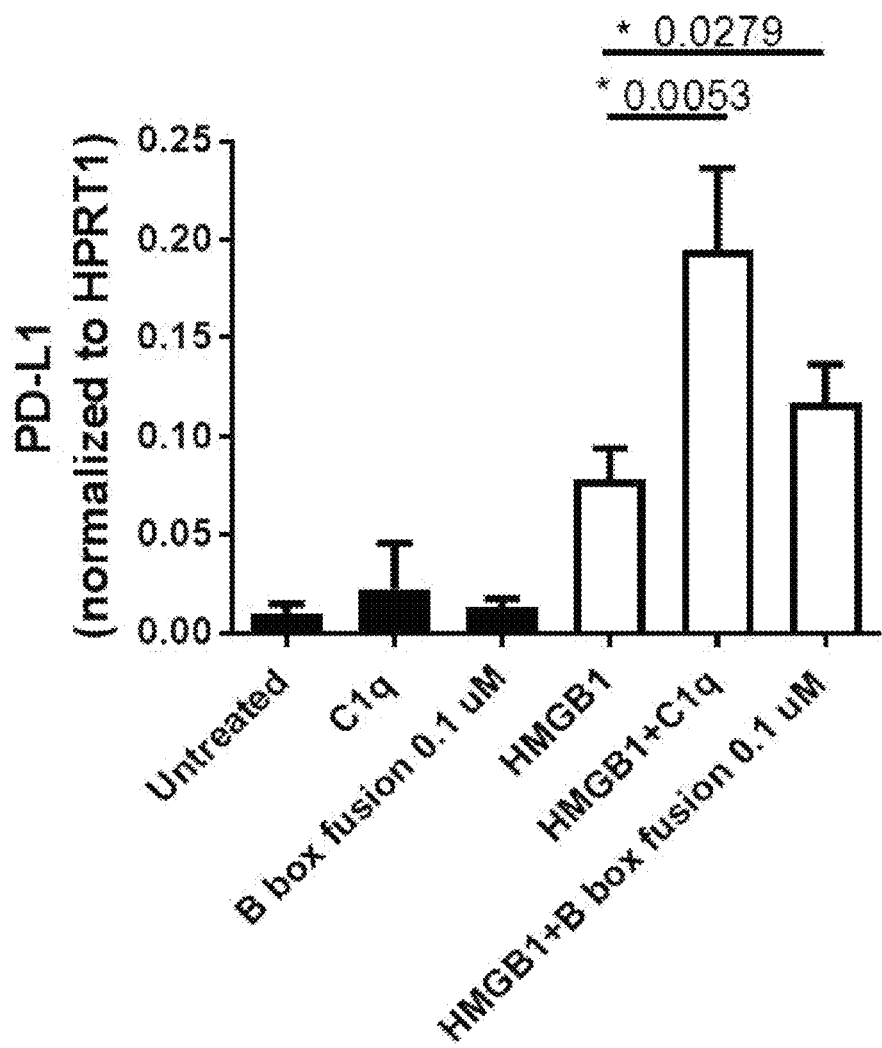

FIG. 16: Fusion protein induces PDL-1.

Figure 17:
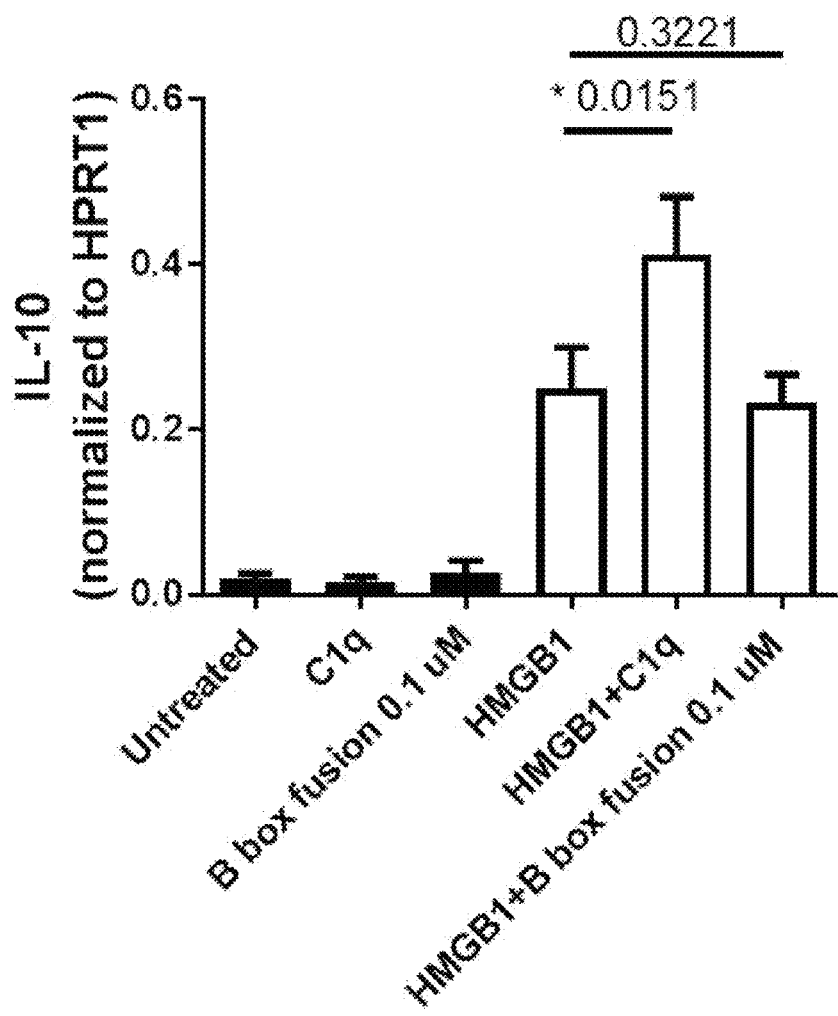

FIG. 17: Fusion protein does not induce IL-10.

Figure 18:
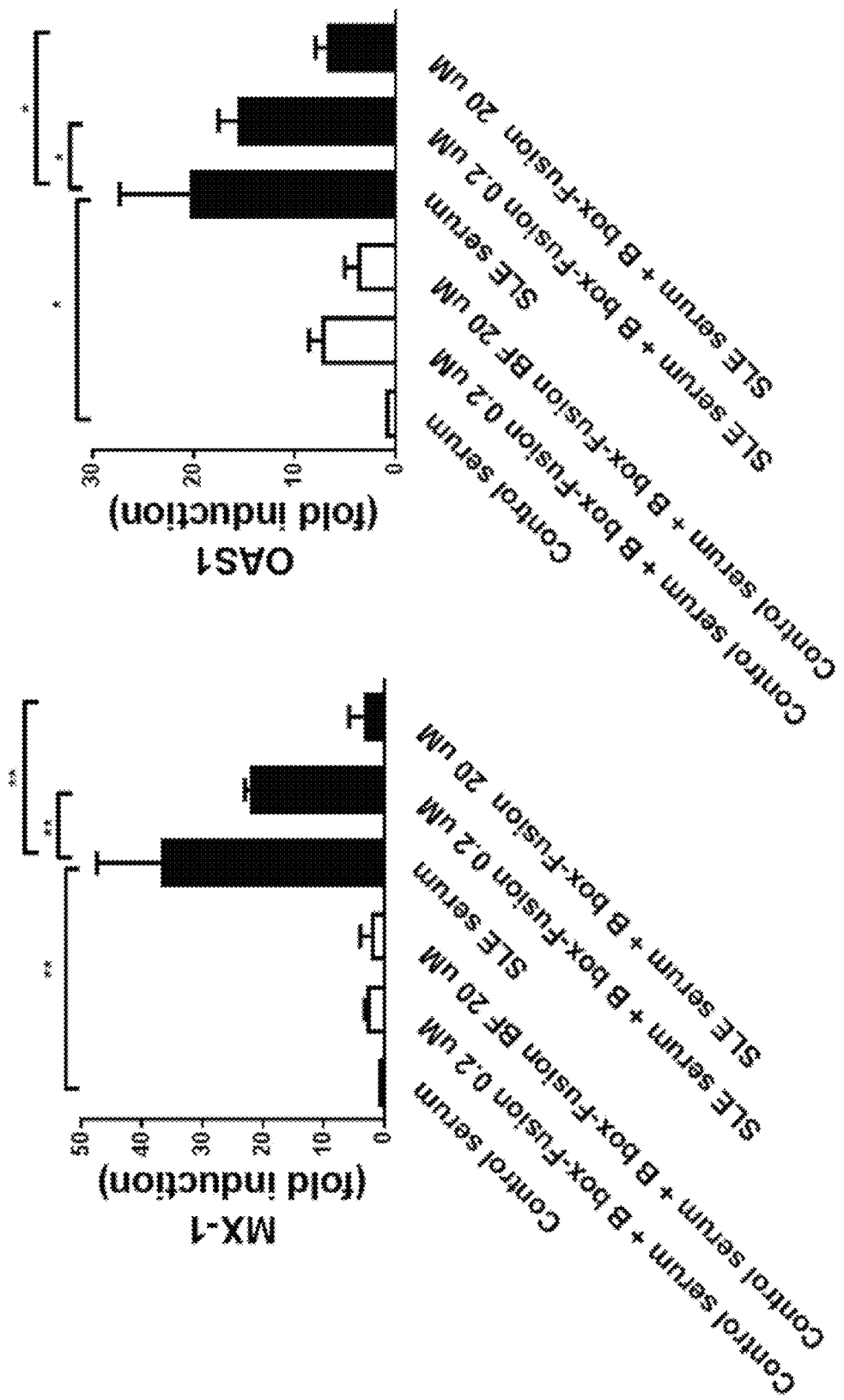

FIG. 18: Left panel shows MX-1 induction levels with each of the listed treatments. Right panel shows OAS1 induction levels in each of the listed conditions.

Figure 19:
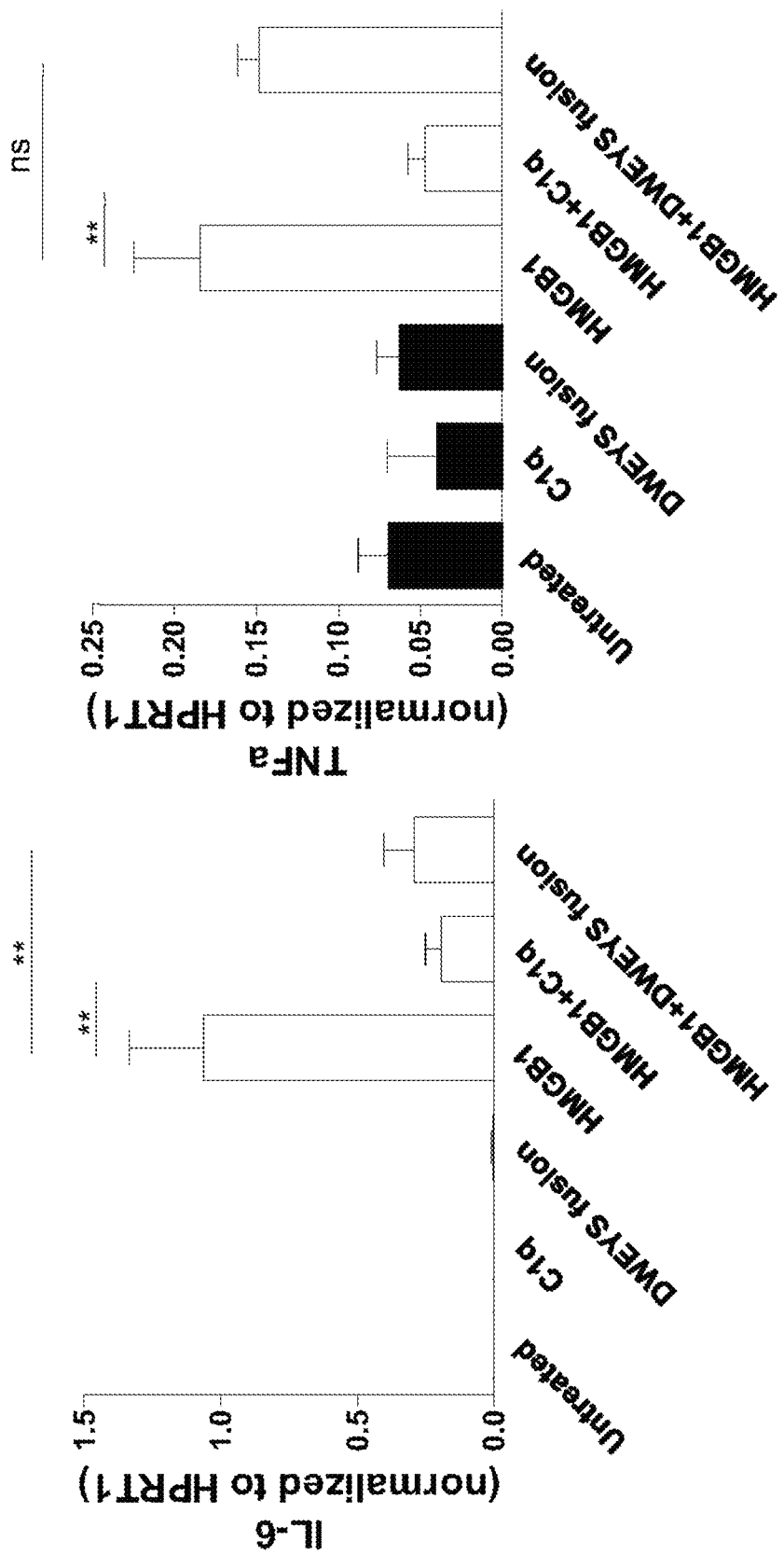

FIG. 19: DWEYS fusion: DWEYS linker C1qa. Left panel shows IL-6 levels after each of the listed treatments. Right panel shows TNF-alpha levels after each of the listed treatments.

Figure 20:
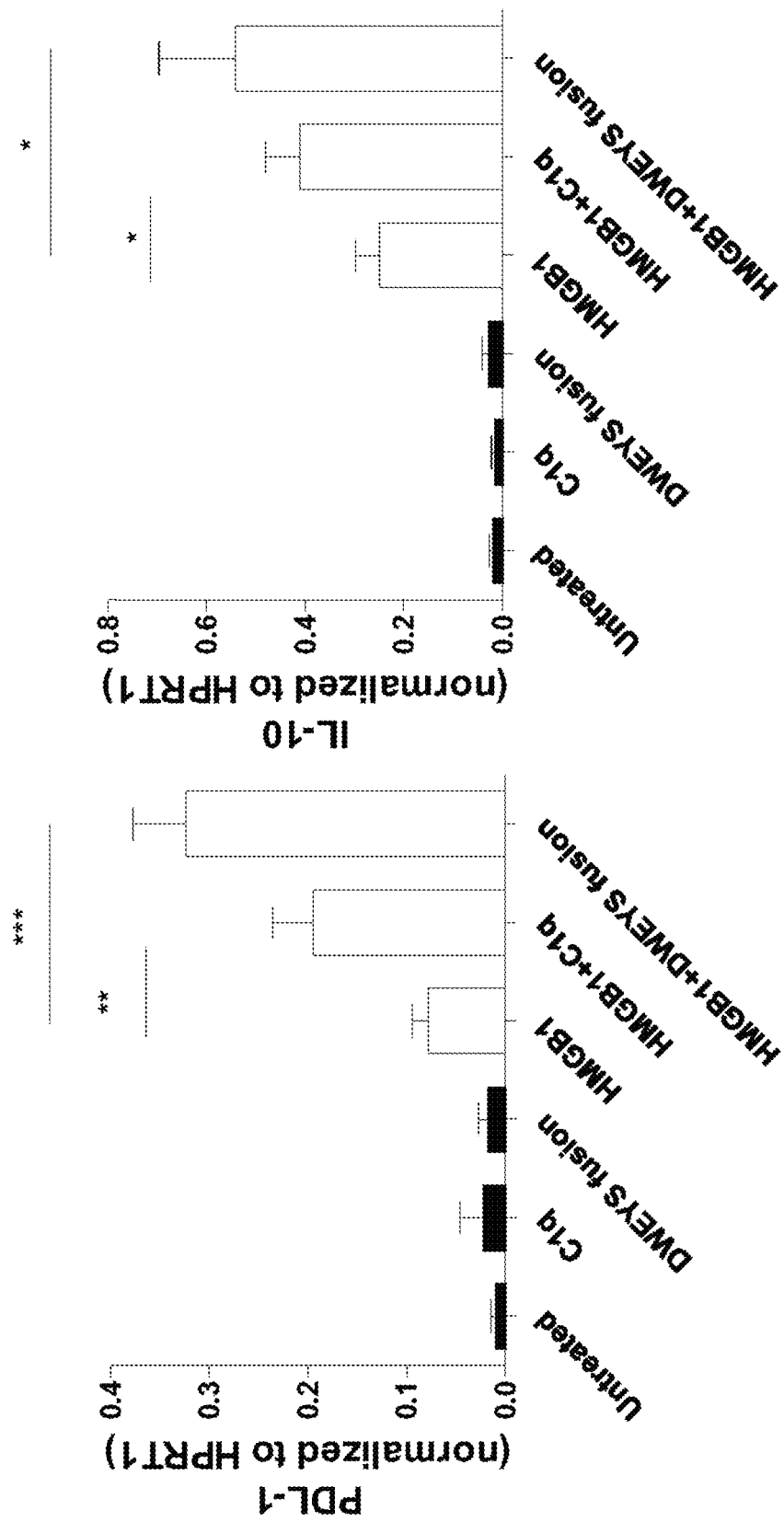
Figures 21A, 21B, 21C, 21D:
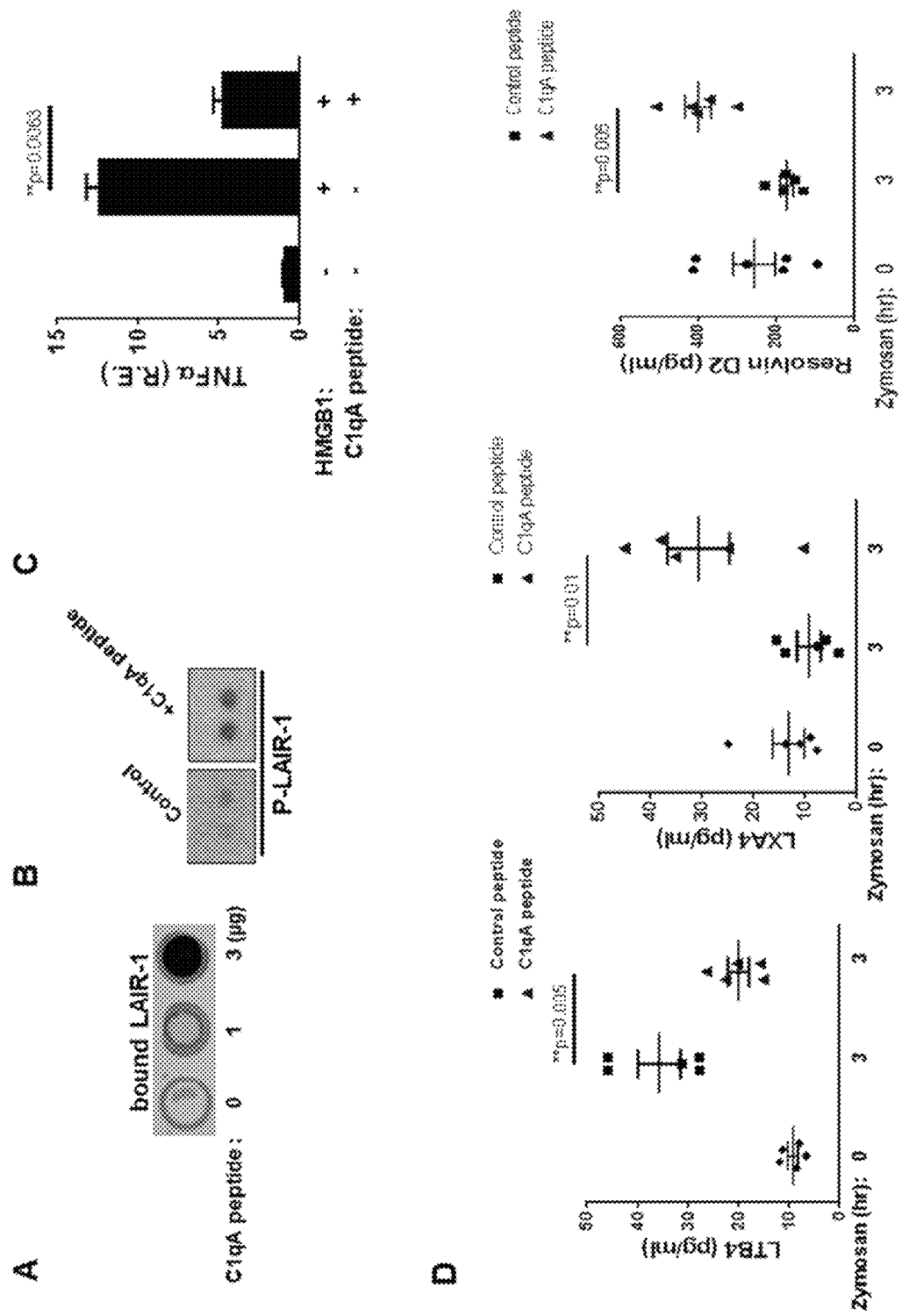

FIG. 20: DWEYS fusion: DWEYS linker C1qa. Left panel shows PDL-1 levels after each of the listed treatments. Right panel shows IL-10 levels after each of the listed treatments.

FIG. 21A-FIG. 21D: LAIR-1-mediated inhibition of C1qA peptide.

Figure 22:
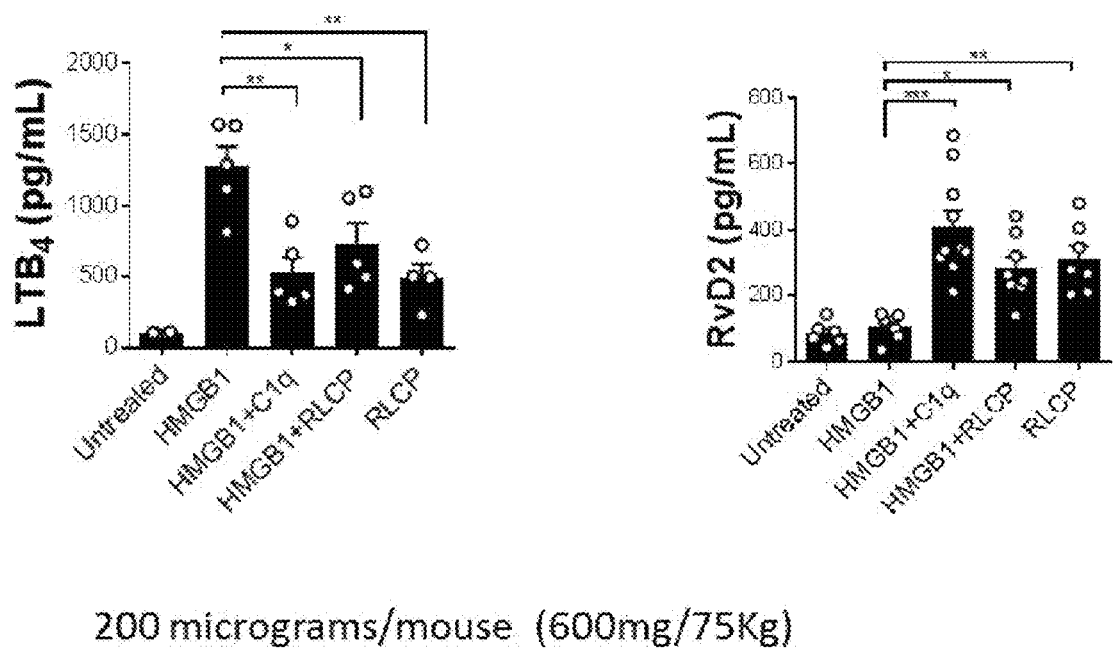

FIG. 22: RAGE and LAIR-1 cross-linking peptide ("RLCP") (KLKEKYEKDIAAYRAKGKPDAAKKGVV-KAEKSKKGGGGSGGGGSGGGGSKGEQ GEPGAPGI or HMGB1 B box-linker-C1q peptide; SEQ ID NO:7) induces RvD2 and abolishes LTB4 induction in murine macrophages by HMGB1 in vivo.

Figure 23:
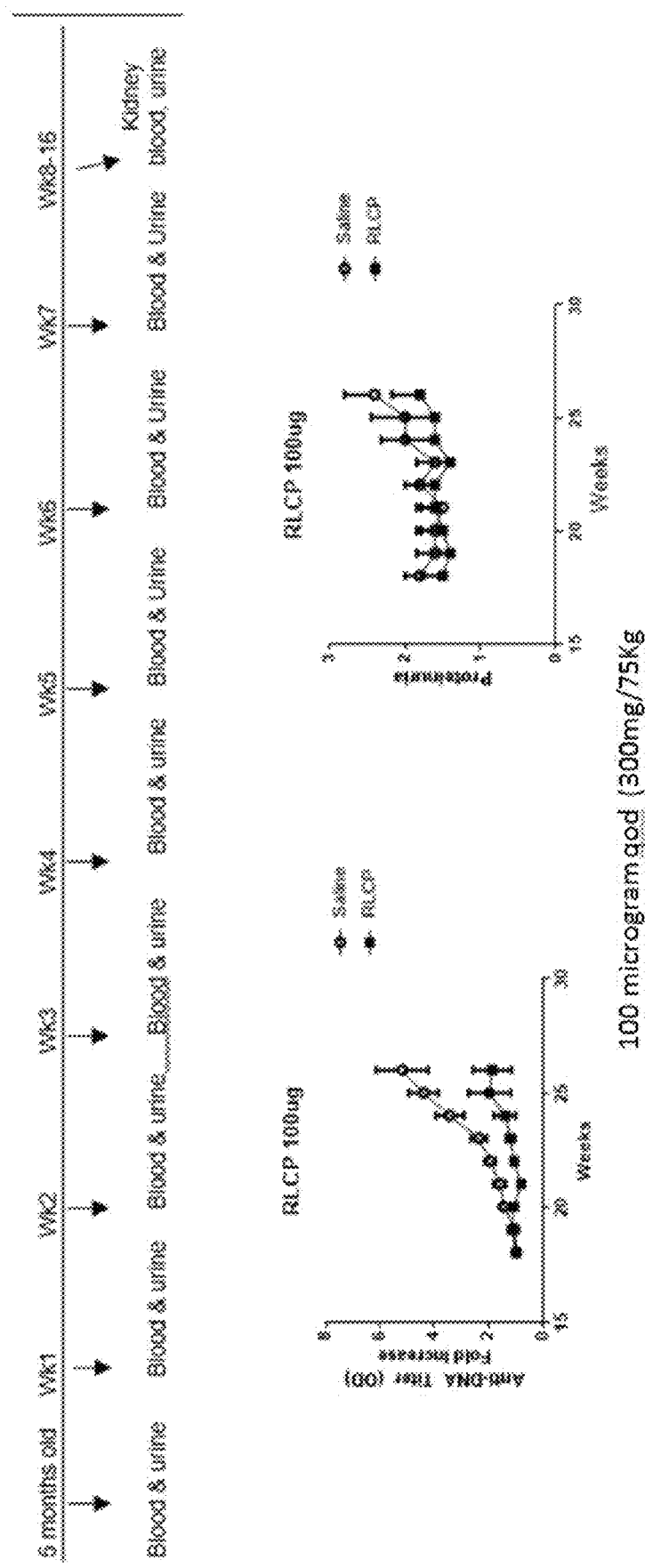

FIG. 23: RLCP slows the progression serum anti-dsDNA antibodies in NZB/W mice in vivo.

Figure 24:
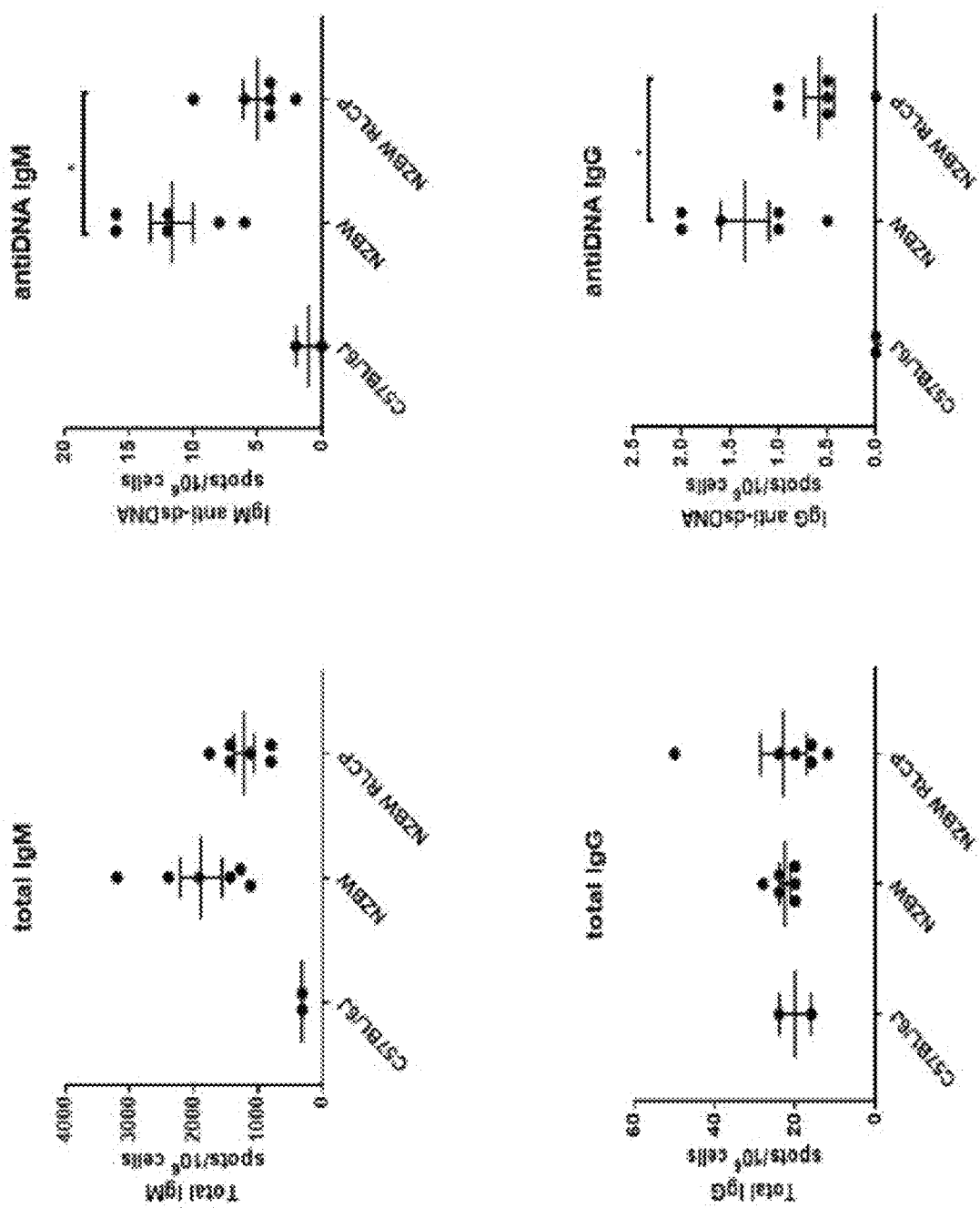

FIG. 24: RLCP decreases anti-DNA IgM/IgG-producing splenocytes in NZB/W mice in vivo.

Figure 25:
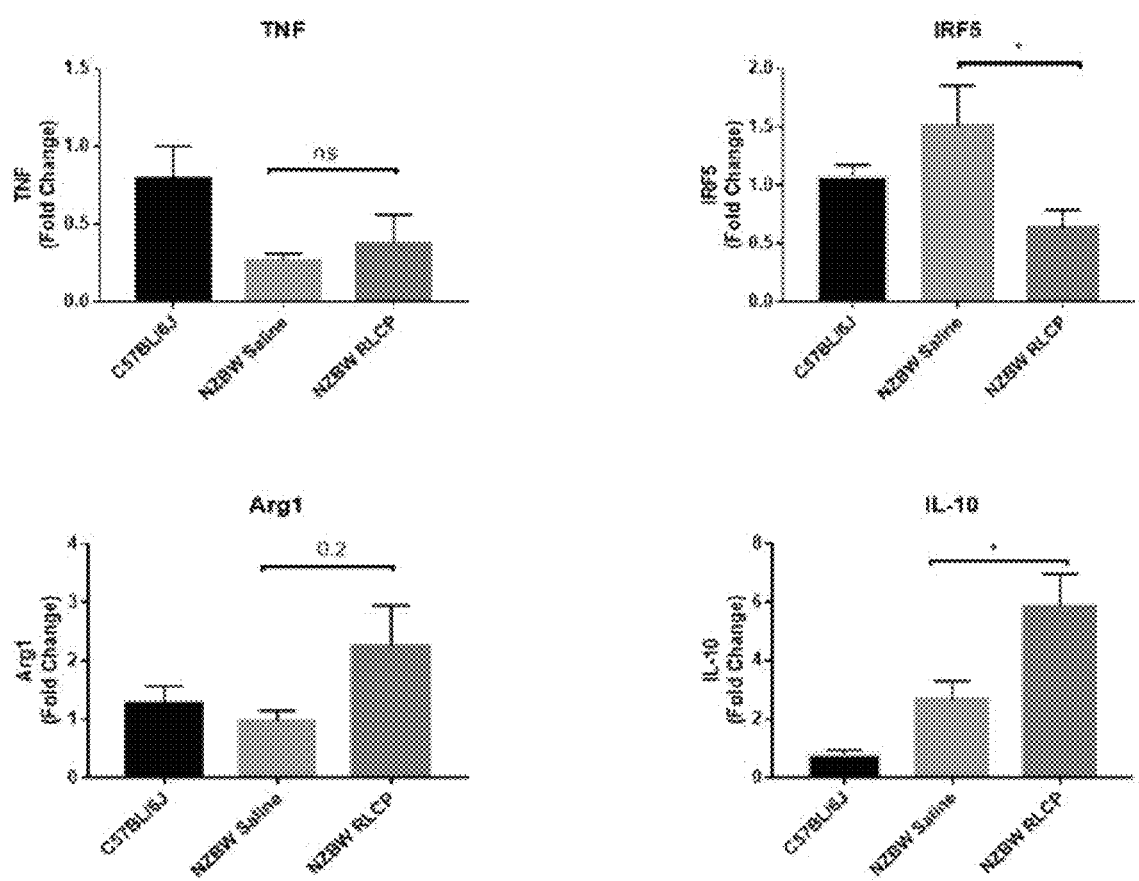

FIG. 25: RLCP decreases inflammatory and increases anti-inflammatory markers in NZB/W splenocytes in vivo. RLCP decreases kidney IgG deposition in NZB/W mice (staining data not shown).

DETAILED DESCRIPTION OF THE INVENTION

A method is provided of cross-linking LAIR-1 and RAGE in a subject comprising contacting the LAIR-1 and RAGE with a composition administered to the subject that binds to LAIR-1 and RAGE comprising a polypeptide.

In embodiments, the LAIR-1 and RAGE are present on a monocyte, and wherein cross-linking LAIR-1 and RAGE mediates monocyte M2 differentiation.

In embodiments, the polypeptide comprises (i) a C1q dodecamer peptide, or a C1q nonamer peptide wherein the nonamer peptide comprises KGEQGEPGA (SEQ ID NO:5), and (ii) a HMBG1 A-box peptide or a HMBG1 B-box peptide.

In embodiments, the LAIR-1 and RAGE are present on a monocyte, and wherein cross-linking LAIR-1 and RAGE effects one or more of (i) dephosphorylation of RAGE, (ii) recruitment of SHP-1 to LAIR-1, and (iii) NF-κB signaling pathway inhibition.

In embodiments, the polypeptide comprises SEQ ID NO:7.

In embodiments, the polypeptide comprises SEQ ID NO:10.

In embodiments, the polypeptide comprises (i) a C1q dodecamer peptide, or a C1q nonamer peptide wherein the nonamer peptide comprises KGEQGEPGA (SEQ ID NO:5), and (ii) a DWEYS peptide (SEQ ID NO:8).

In embodiments, the polypeptide comprises SEQ ID NO:11.

In embodiments, the composition comprises a bispecific antibody directed to LAIR-1 and to RAGE. In an embodiment, the bispecific antibody is capable of cross-linking LAIR-1 and RAGE when bound thereto. In an embodiment, the bispecific antibody cross-links a LAIR-1 and a RAGE when bound to both.

In embodiments, the bispecific antibody is a BsDb (bispecific diabody), scBsDb (single-chain bispecific diabody), scBsTaFv (single-chain bispecific tandem variable domain), or a BssdAb (bispecific single-domain antibody). In embodiments, the bispecific antibody does not comprise an Fc region. In embodiments, the bispecific antibody comprises an Fc region. Bispecific antibodies can be made by many methods including via recombinant technology and e.g., Ig-scFv fusion, diabody-Fc fusion, dual-variable-domain-IgG (DVD-IgG) fusion techniques, and "knobs-into-holes BsAb IgG" technology.

A polypeptide is provided comprising (i) a C1q dodecamer peptide, or a C1q nonamer peptide wherein the nonamer peptide comprises KGEQGEPGA (SEQ ID NO:5), and (ii) a HMBG1 A-box peptide or a HMBG1 B-box peptide.

A C1q dodecamer peptide is a peptide comprising the sequence KGEQGEPGAPGI (SEQ ID NO:3). A C1q nonamer peptide is a peptide comprising the sequence KGEQGEPGA (SEQ ID NO:5). A HMBG1 A-box peptide is a peptide comprising the sequence MGKGDPKKPRGKMSSYAFFVQT (SEQ ID NO:1). A HMBG1 B-box peptide is a peptide comprising the sequence KLKEKYEKDIAAYRAKGKPDAAKKGVVKAEKSKK (SEQ ID NO:2). In an embodiment, the polypeptide is recombinantly produced. In an embodiment, the polypeptide is a recombinantly produced fusion protein. A nucleic acid, encoding the polypeptide comprising (i) a C1q dodecamer peptide, or a C1q nonamer peptide wherein the nonamer peptide comprises KGEQGEPGA (SEQ ID NO:5), and (ii) a HMBG1 A-box peptide or a HMBG1 B-box peptide, is also provided. In an embodiment, the nucleic acid is recombinantly produced. In an embodiment, the nucleic acid is a cDNA.

In an embodiment, the polypeptide comprising the C1q dodecamer peptide, or C1q nonamer peptide, and the HMBG1 A-box peptide or HMBG1 B-box peptide is up to 70 amino acids in length. In an embodiment, the polypeptide is up to 65 amino acids in length. In an embodiment, the polypeptide is up to 60 amino acids in length.

In an embodiment of the polypeptide, the carboxy terminal amino acid or the amino terminal amino acid residue of the C1q dodecamer or nonamer is bound to the amino terminal amino acid or the carboxy terminal amino acid residue, respectively, of the HMBG1 A-box or HMBG1 B-box peptide.

In an embodiment of the polypeptide, the C1q dodecamer or nonamer is bound directly by a peptide bond to the HMBG1 A-box or HMBG1 B-box peptide.

In an embodiment of the polypeptide, the C1q dodecamer or nonamer is bound by a peptide bond to a linker peptide which is bound by a peptide bond to the HMBG1 A-box or HMBG1 B-box peptide. In an embodiment of the polypeptide, the linker peptide comprises (GGGGS)n or A(EAAAK)nA (where n=2, 3, 4, or 5). In an embodiment the linker comprises (Gly$_4$Ser)$_3$. In an embodiment, the linker is rigid. In an embodiment the linker is cleavable. Non-limiting examples of cleavable linkers within the scope of the invention include disulfide links and protease cleavable linkers. In a preferred embodiment, the linker is a peptide linker.

In an embodiment the polypeptide further comprises a plasma half-life extending moiety. In an embodiment, the plasma half-life extending moiety is covalently attached to the polypeptide. Plasma half-life extending moieties are well known in the art, such as PEG molecules, fatty acids bound to peptide side chains, further polypeptides such as Fc, human serum albumin, XTEN and PAS. In an embodiment, the polypeptide further comprising an immunoglobulin Fc monomer or dimer. In an embodiment, the polypeptide does not further comprise a plasma half-life extending moiety. In an embodiment, the polypeptide does not further comprise an immunoglobulin Fc. In an embodiment, the polypeptide does further comprise an immunoglobulin Fc. In an embodiment, the immunoglobulin Fc is an immunoglobulin G Fc. In an embodiment, the immunoglobulin Fc has the sequence of a human immunoglobulin Fc. In an embodiment, the immunoglobulin Fc has the sequence of a human immunoglobulin IgG1 Fc. Human immunoglobulin IgG1 Fc are well known in the art and are readily and routinely identified by those of skill in the art. Automatic sequences can be used for such and widely-available alignment matching tools. In an embodiment of the Fc, the Fc is de-fucosylated of one or more N-linked oligosaccharides on the Fc region. In an embodiment, the polypeptide does not further comprise a plasma half-life extending entity.

In an embodiment, the polypeptide comprises the HMBG1 A-box. In an embodiment, the HMBG1 A-box comprises a 22-amino acid residue sequence. In an embodiment, the HMBG1 A-box comprises MGKGDPKK PRGKMSSYAFFVQT (SEQ ID NO:1). In an embodiment, the polypeptide comprises MGKGDPKKP RGKMSSYA FFVQTGGGGSGGGGSGGGGSKGEQGEPGAPGI (SEQ ID NO:10).

In an embodiment, the polypeptide comprises the HMBG1 B-box. In an embodiment, the HMBG1 B-box comprises a 34-amino acid residue sequence. In an embodiment, the HMBG1 B-box comprises KLKEKYEKDIAAY-RAKGKPDAAKKGVVKAEKSKK (SEQ ID NO:2). In an embodiment, the polypeptide comprises the sequence KLKEKYEKDIAAYRAKGKPDAAKKGVVKAEKSKK GGGGSGGGGSGGGGSKGEQ GEPGAPGI (SEQ ID NO:7).

In an embodiment, the polypeptide comprises the C1q dodecamer peptide which has the sequence KGEQGEP-GAPGI (SEQ ID NO:3).

In an embodiment, the polypeptide comprises the C1q nonamer peptide but not the C1q dodecamer peptide which has the sequence KGEQGEPGAPGI (SEQ ID NO:3).

In an embodiment, the polypeptide does not comprise a mouse C1q nonamer sequence.

Also provided is a method of treating an autoimmune inflammatory condition comprising administering an amount of a polypeptide as described herein effective to treat an autoimmune inflammatory condition.

In an embodiment, the autoimmune inflammatory condition is systemic lupus erythematosus (SLE). In an embodiment, the autoimmune inflammatory condition is rheumatoid arthritis.

Also provided is a method to quiesce a monocyte in a subject comprising administering an amount of the polypeptide as described herein effective to quiesce a monocyte in a subject.

Also provided is a method to induce an M2 phenotype in a monocyte in a subject and/or reduce an adaptive immune activation in a subject comprising administering to the subject an amount of the polypeptide as described herein effective to induce M2 phenotype in a monocyte in a subject and/or reduce an adaptive immune activation in a subject.

Also provided is a method of reducing a hyper-activated innate immune response in a subject comprising administering an amount of the polypeptide as described herein effective to treat reduce a hyper-activated innate immune response.

Also provided is a polypeptide comprising (i) a C1q dodecamer peptide, or a C1q nonamer peptide wherein the nonamer peptide is KGEQGEPGA (SEQ ID NO:5), and (ii) a DWEYS peptide. In an embodiment, the DWEYS peptide consists of DWEYS (SEQ ID NO:8).

In an embodiment, the C1q dodecamer or nonamer is bound by a peptide bond to a linker peptide which is bound by a peptide bond to the DWEYS peptide. In an embodiment, the linker peptide comprises (GGGGS)n or A(EAAAK)nA (where n=2, 3, 4, or 5). In an embodiment, polypeptide has the sequence DWEYSGGGGSGGGGS GGGGSKGEQGEPGAPGI (SEQ ID NO:11).

In an embodiment, the polypeptide further comprises a plasma half-life extending entity. In an embodiment, the plasma half-life extending entity is covalently attached to the polypeptide. Plasma half-life extending entities are well known in the art, such as PEG molecules, fatty acids bound to peptide side chains, further polypeptides such as Fc, human serum albumin, XTEN and PAS. In an embodiment, the polypeptide further comprising an immunoglobulin Fc monomer or dimer. In an embodiment, the polypeptide does not further comprise a plasma half-life extending entity. In an embodiment, the immunoglobulin Fc is an immunoglobulin G Fc. In an embodiment, the immunoglobulin Fc has the sequence of a human immunoglobulin Fc. In an embodiment, the immunoglobulin Fc has the sequence of a human immunoglobulin IgG1 Fc. In an embodiment of the Fc, the Fc is de-fucosylated of one or more N-linked oligosaccharides on the Fc region. In an embodiment, the polypeptide does not further comprise a plasma half-life extending entity.

In an embodiment, the C1q dodecamer peptide has the sequence KGEQGEPGAPGI (SEQ ID NO:3). In an embodiment, the polypeptide comprises the C1q nonamer peptide but not the C1q dodecamer peptide having the sequence KGEQGEPGAPGI (SEQ ID NO:3).

In an embodiment, the polypeptide does not comprise a mouse C1q nonamer sequence.

Also provided is a method of treating an autoimmune inflammatory condition comprising administering an amount of the polypeptide as described herein comprising the DWEYS peptide effective to treat an autoimmune inflammatory condition.

In an embodiment, the autoimmune inflammatory condition is systemic lupus erythematosus (SLE). In an embodiment, the autoimmune inflammatory condition is rheumatoid arthritis.

Also provided is a method of treating an inflammatory condition in sepsis comprising administering an amount of the polypeptide as described herein comprising the DWEYS peptide effective to treat an inflammatory condition in sepsis.

Also provided is a method of maintaining a systemic lupus erythematosus (SLE) remission state in a subject having had SLE but in remission, comprising administering an amount of the polypeptide as described herein comprising the DWEYS peptide effective to maintain a remission state in a subject having had systemic lupus erythematosus.

Also provided is a method of reducing a hyper-activated innate immune response in a subject comprising administering an amount of the polypeptide as described herein comprising the DWEYS peptide effective to treat reduce a hyper-activated innate immune response.

In an embodiment of the methods described herein, the subject is a human.

In an embodiment of the methods and polypeptides described herein, the C1q peptide has a sequence identical to a portion of human C1q having the sequence:

```
                                        (SEQ ID NO: 4)
MEGPRGWLVLCVLAISLASMVTEDLCRAPDGKKGEAGRPGRRGRPGLKGEQ

GEPGAPGIRTGIQGLKGDQGEPGPSGNPGKVGYPGPSGPLGARGIPGIKGT

KGSPGNIKDQPRPAFSAIRRNPPMGGNVVIFDTVITNQEEPYQNHSGRFVC

TVPGYYYFTFQVLSQWEICLSIVSSSRGQVRRSLGFCDTTNKGLFQVVSGG

MVLQLQQGDQVWVEKDPKKGHIYQGSEADSVFSGFLIFPSA.
```

In an embodiment, the C1q peptide comprises the sequence KGEQGEPGA (SEQ ID NO:5).

In an embodiment, the C1q peptide comprises the sequence KGEQGEPGAPGI (SEQ ID NO:3).

In an embodiment, the C1q peptide comprises the sequence KGEQGEPGA (SEQ ID NO:5) but not KGEQGEPGAPGI (SEQ ID NO:3).

In an embodiment, the C1q peptide comprises the sequence KGEQGEPGA KGEQGEPGAPGI (SEQ ID NO:6).

In an embodiment of the methods described herein, the polypeptide can be administered as an active ingredient in a pharmaceutical composition. In an embodiment, the polypeptide is the only pharmaceutically active ingredient in the pharmaceutical composition. In an embodiment, the pharmaceutical composition comprises a pharmaceutical carrier.

In the methods described herein, administration of the polypeptide, or of a pharmaceutical composition comprising the polypeptide, can be auricular, buccal, conjunctival, cutaneous, subcutaneous, endocervical, endosinusial, endotracheal, enteral, epidural, via hemodialysis, interstitial, intra-abdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, uretheral, and vaginal.

As used herein, "treating" an autoimmune disease means that one or more symptoms of the disease, such as inflammation or other parameters by which the disease is characterized, are reduced, ameliorated, prevented, placed in a state of remission.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

This disclosure reveals interactions of two proteins that are dysregulated in SLE: High Mobility Group Box 1 (HMGB1) and the first component of complement (C1q). HMGB1 is an evolutionarily ancient DNA-binding nucleoprotein found in almost all mammalian cells (3,4). In addition to its role as a transcriptional regulator, HMGB1 also functions as a Damage-Associated Molecular Pattern (DAMP) molecule when either released from necrotic cells (passive release) or secreted from activated leukocytes such as monocytes, macrophages and myeloid dendritic cells (active release) (5,6). HMGB1 is significantly elevated in the serum from patients with SLE, where its role as a necessary co-factor for activation of endosomal TLRs is believed to be critical in lupus pathogenesis (4). HMGB1 is a ligand for the Receptor for Advanced Glycation Endproducts (RAGE), and functions to transport RNA and DNA to endosomal TLRs, leading to production of type 1 interferon (IFN), IFN-inducible genes and pro-inflammatory cytokines (6-8). Administration of antibodies against HMGB1 confers significant protection against tissue injury in experimental models of autoimmune disease and inflammation (3). Selective deletion of HMGB1 reduced survival of mice in a sepsis model (9). HMGB1 has also been shown to suppress inflammation (10), promote the regeneration of skin grafts in mice (11) and enhance ATP production in pancreatic tumor cell lines (12,13). Although HMGB1 is the subject of intense investigation, we are still learning about this protein and how it elicits both positive and negative immune responses.

Post-translational modification of HMGB1 significantly influences the biological activity of this molecule (3). One post-translational modification that dramatically affects the activity of HMGB1 is the redox state of three critical cysteine residues (4). Disulfide HMGB1, bearing a disulfide bond between C23 and C45, with a free cysteine at C106, binds the TLR4 co-receptor MD2 (14). Reduced HMGB1, which bears three fully reduced cysteine thiol residues, on the other hand, signals through CXCR4 to mediate chemokine-like activity. Finally, sulfonyl HMGB1, which contains a sulfonyl group on any of the cysteines, has no activity for cell migration or cytokine induction.

Since HMGB1 is an evolutionarily conserved molecule which predates the development of adaptive immunity, other ancient proteins were investigated as possible HMGB1 regulatory factors within the scope of innate immunity. C1q is a 460 kDa protein formed by six homotrimeric subunits containing an N-terminal collagen-like sequence and a C-terminal globular region (15). In addition to its role in initiating the complement cascade, C1q has long been known to possess immunoregulatory properties (16,17). C1q binds to molecular pattern molecules derived from pathogens and endogenous damage associated molecules, including antibody-antigen complexes, bacterial toxins, myelin, and 13 amyloid 18. Patients with active SLE have lower levels of C1q because the immune complex formation in SLE consumes complement components and because SLE patients produce antibodies that target and remove C1q (19). Although rare, C1q deficiency is the strongest genetic risk factor for developing SLE (20,21).

Recently, it was determined that Leukocyte-Associated Ig-like Receptor 1 (LAIR-1; CD305), a transmembrane protein Ig superfamily member, is a high-affinity receptor for C1q (22). Binding of C1q to LAIR-1 mediates inhibition of monocyte-to-dendritic cell (DC) differentiation and plasmacytoid DC (pDC) activation, functions that help explain the contribution of C1q deficiency to SLE pathogenesis.

It was investigated whether the mechanism by which C1q interacts with LAIR-1 to inhibit immune responses may provide insight into the activity of both HMGB1 and C1q in SLE. The results disclosed herein illuminate a specific previously unknown C1q-HMGB1 interaction: C1q binds to disulfide HMGB1, catalyzing formation of a multimeric protein complex comprising HMGB1, C1q, LAIR-1 and RAGE. This multimeric complex triggers monocytes to differentiate into an M2 phenotype, upregulating the expression of several anti-inflammatory molecules (e.g., Programmed Death Ligand-1 (PDL-1), Mer tyrosine-kinase (Mer), Interleukin-10 (IL-10), and effectively limits the differentiation of monocytes into dendritic cells (DCs), blocking the downstream adaptive immune response. These findings identify a mechanism by which C1q levels modulate HMGB1's inflammatory activity to achieve immuneregulation, a mechanism that is impaired in SLE due to genetic or acquired C1q deficiency.

Figure 1A:
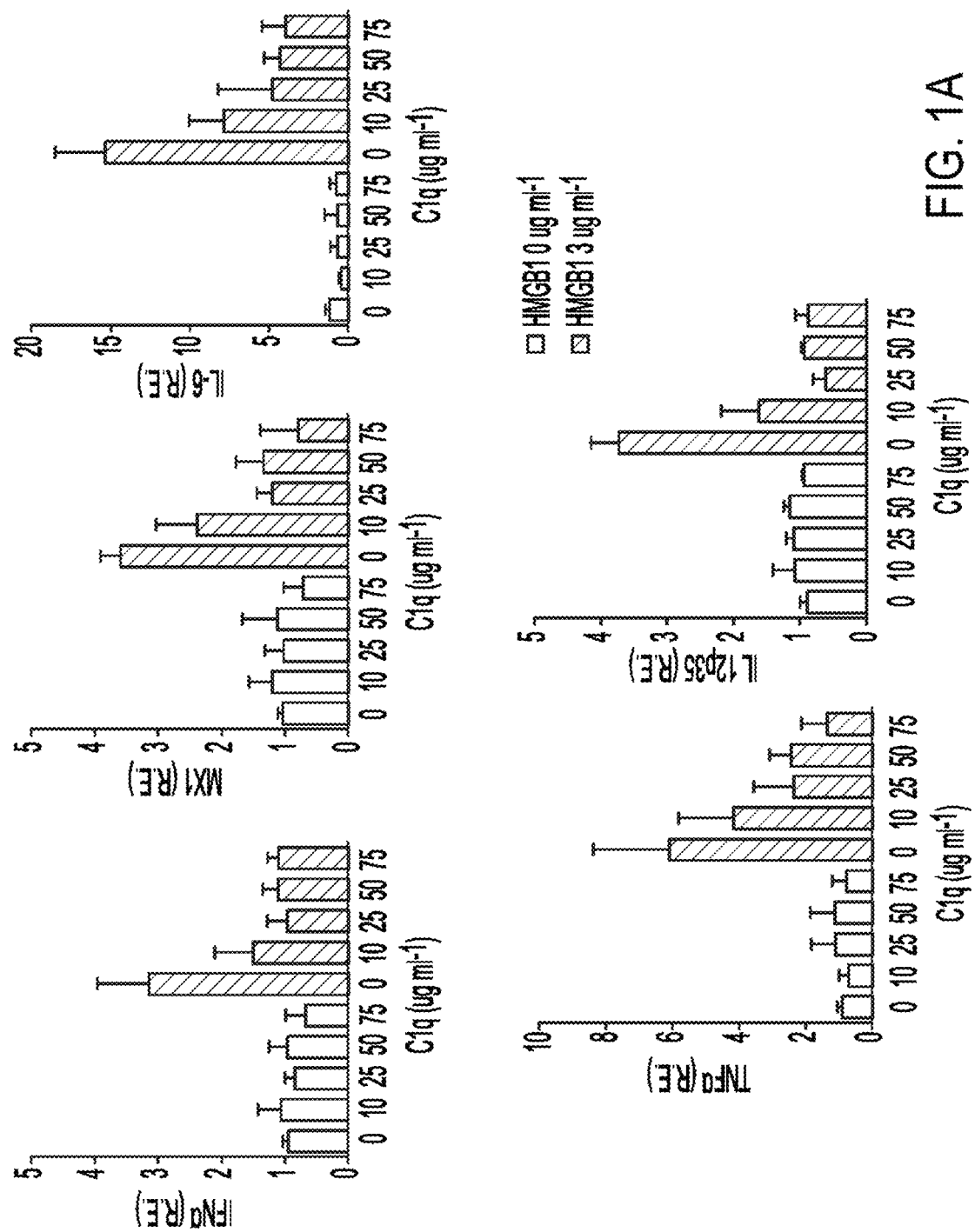
FIG. 1A-FIG. 1G. C1q inhibits expression of HMGB1-induced IFNα, MX1 and inflammatory cytokines by human monocytes. (1A) mRNA levels for IFNα, MX1, IL-6, TNFα and IL12p35 in monocytes stimulated with or without HMGB1 (3 µg/ml) and various concentrations of C1q (µg ml-1) for 6 h in serum free medium. (1B) HMGB1 (3 µg/ml) induced IL-6, TNFα and IL12p70 protein production by monocytes which was reduced in the presence of various concentrations of C1q, assessed at 24 h. (1C) Increasing the concentration of HMGB1 (10 µg ml-1) abolished the C1q-mediated inhibition of transcription as assessed by q-PCR and ELISA. (1D) IFNα, MX1, IL-6, TNFα mRNA expression by monocytes transfected with control siRNA or LAIR-1 siRNA and treated with C1q (25 µg/ml), HMGB1 (3 µg/ml) for 6 h. (1E) MX1 and TNFα mRNA expression in monocytes treated with C1q (25 µg/ml), LAIR-2 (20 µg/ml) and HMGB1 (3 µg/ml) for 6 h. (1F) IFNα, IL-6 and TNFα mRNA expression by the adherent cell fraction of peripheral blood mononuclear cells treated with C1q (25 µg/ml), HMGB1 (3 µg/ml) for 6 h. (1G) LAIR-1 deficient monocytes exhibit no C1q-mediated inhibition for IFNα, MX1, IL-6 and TNFα mRNA expression. Data are expressed as fold induction relative to controls (mean±s.d. of triplicates). R.E; relative expression. ELISA data reflect mean±s.d. of duplicate samples. Differences, determined by the unpaired t-test and One-way ANOVA, are: not significant, ns.
Figure 1B:
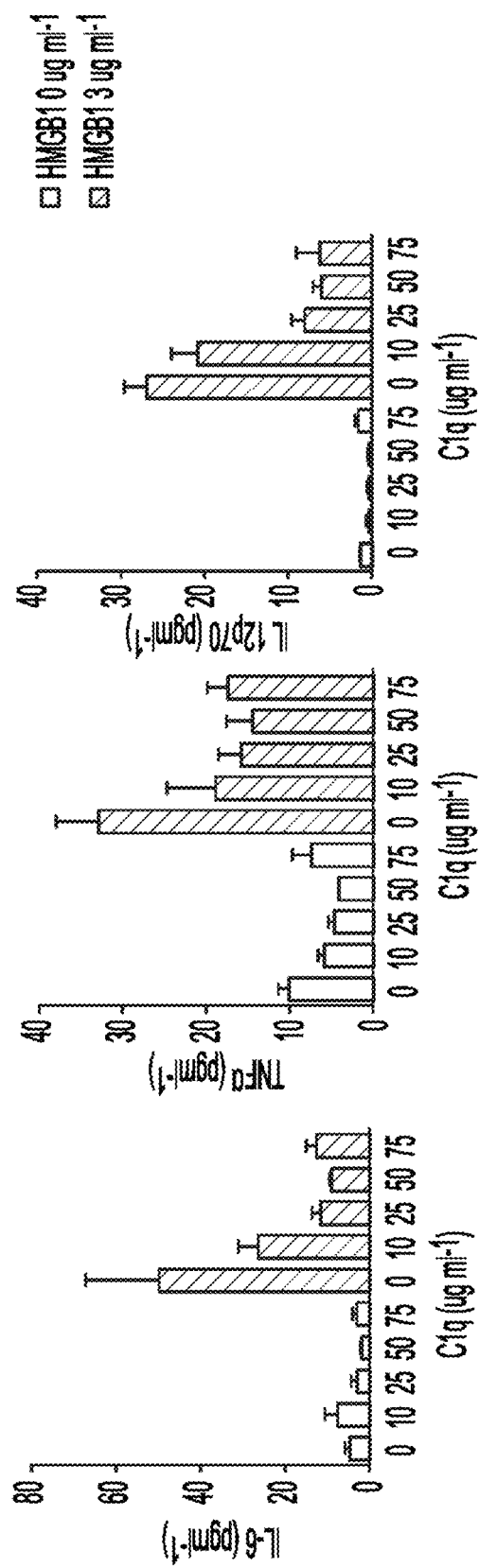
Figure 1C:
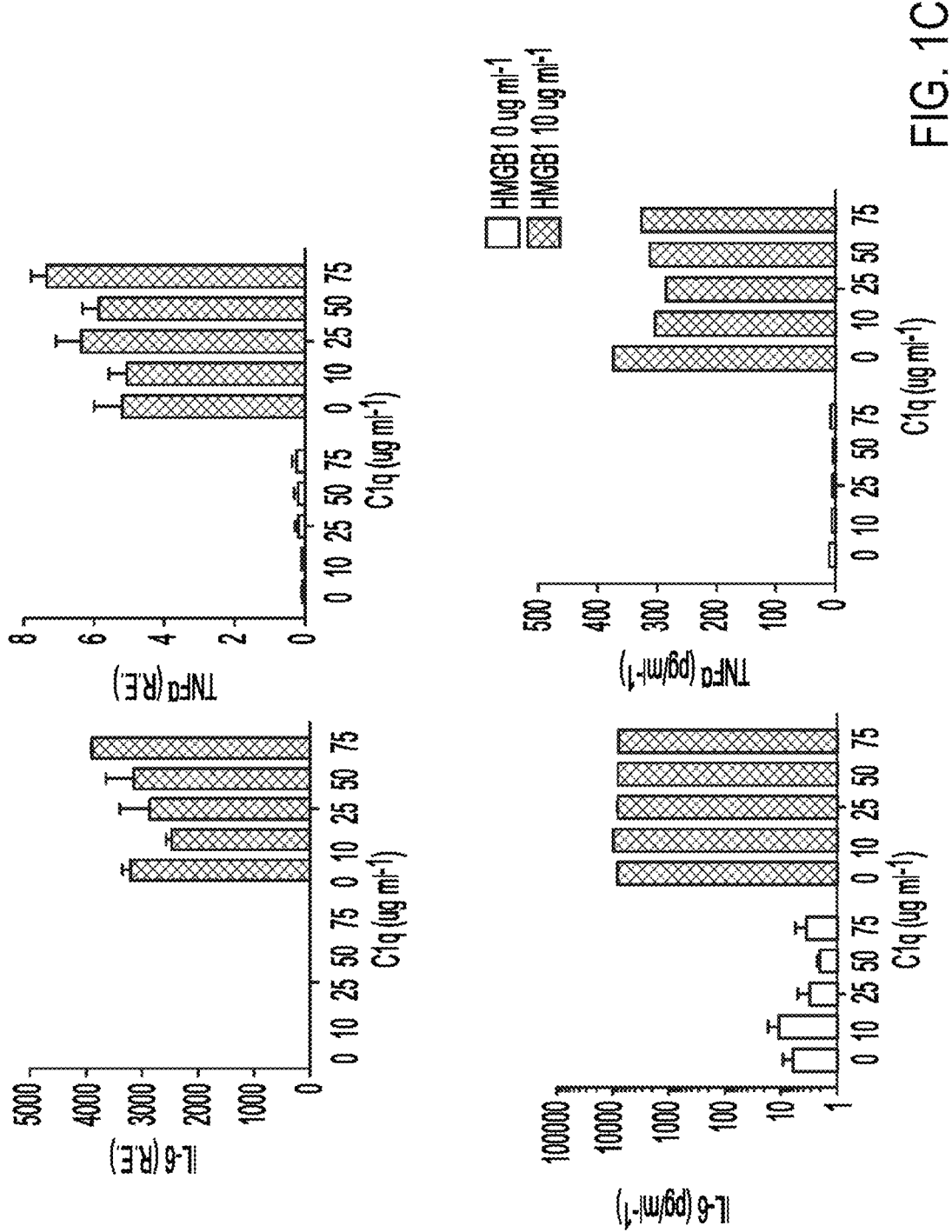

C1q inhibits HMGB1-induced monocyte activation: This laboratory has demonstrated that C1q inhibits the activation of monocytes and plasmacytoid dendritic cells by engaging LAIR-1 (22). It was investigated whether C1q might act through inhibiting the pro-inflammatory activity of HMGB1. To test this hypothesis, cultures of human monocytes isolated from peripheral blood of healthy volunteers were incubated in the presence or absence of HMGB1 with and without C1q and assessed downstream cytokine production. Cultures were performed in serum-free medium to avoid contamination by C1q in serum and permit accurate control of the concentration of C1q. As anticipated, the addition of HMGB1 dramatically increased the transcription and secretion of type 1 IFN, IFN-inducible genes and NFκB-dependent proinflammatory cytokines, generating M1-like macrophages, as has previously been reported (23) (FIG. 1a-b). While C1q did not alter transcription of these genes in the absence of HMGB1, the addition of human C1q to HMGB1 counteracted the HMGB1-mediated cytokine transcription and protein induction in a dose-dependent manner (FIG. 1a-b). Physiologic levels of C1q effectively blocked monocyte activation while levels commonly present in SLE patients (~25-50 µg/ml) were less inhibitory. Increasing the levels of HMGB1 abrogated the inhibitory effect of C1q (FIG. 1c), suspecting that the ratio of C1q to HMGB1 is critical.

Figure 1D:
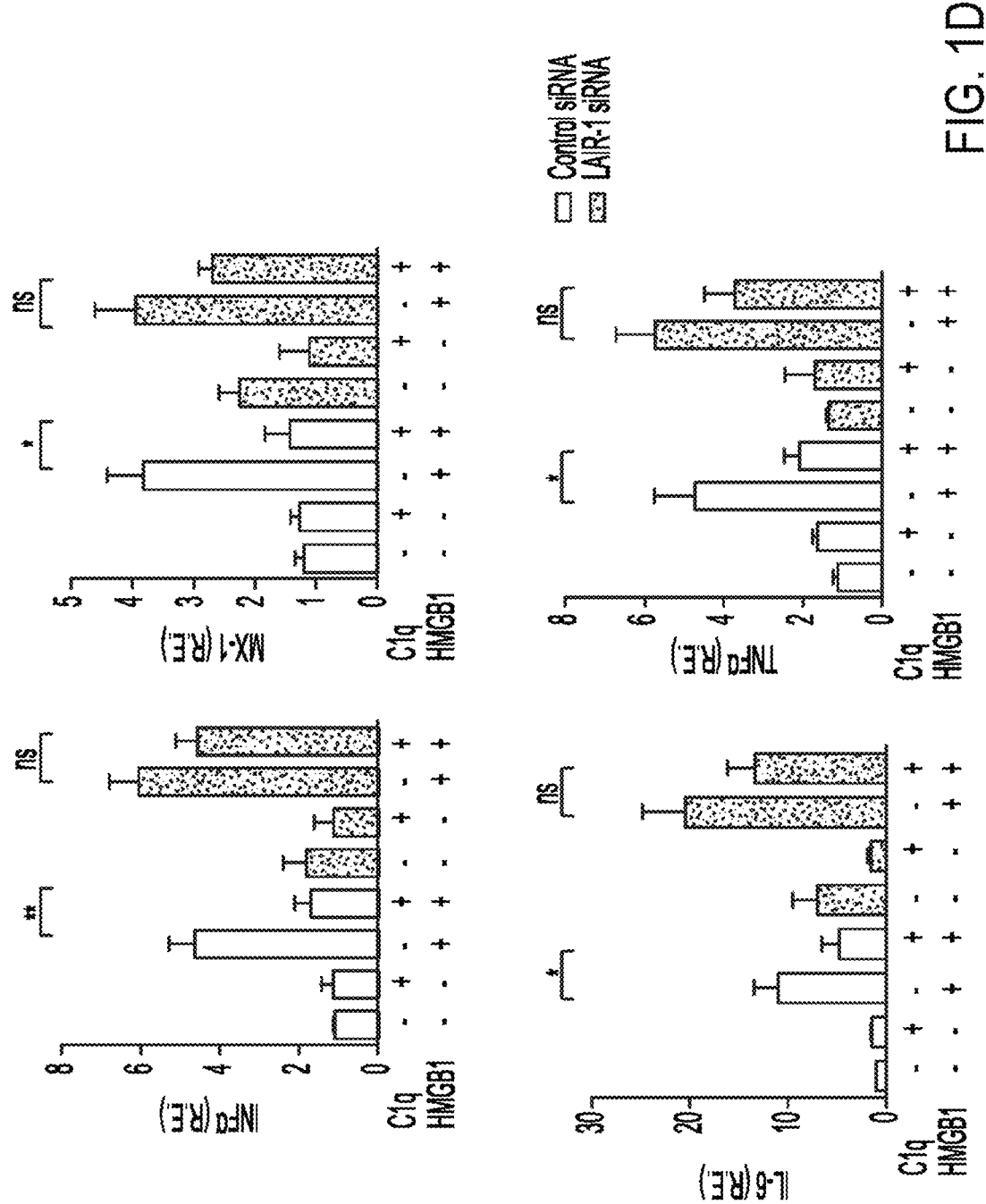
Figure 1E:
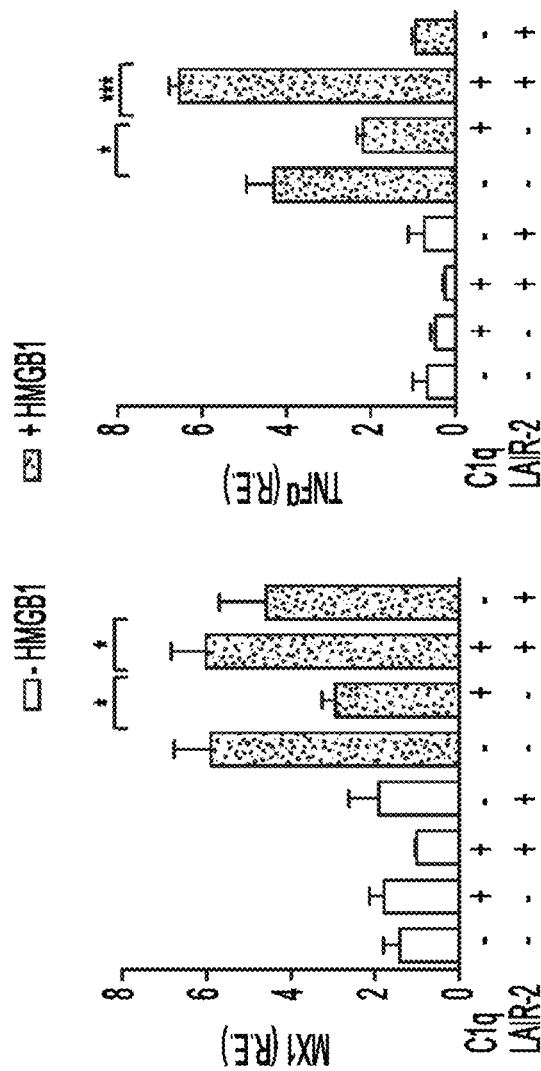
Figure 1F:
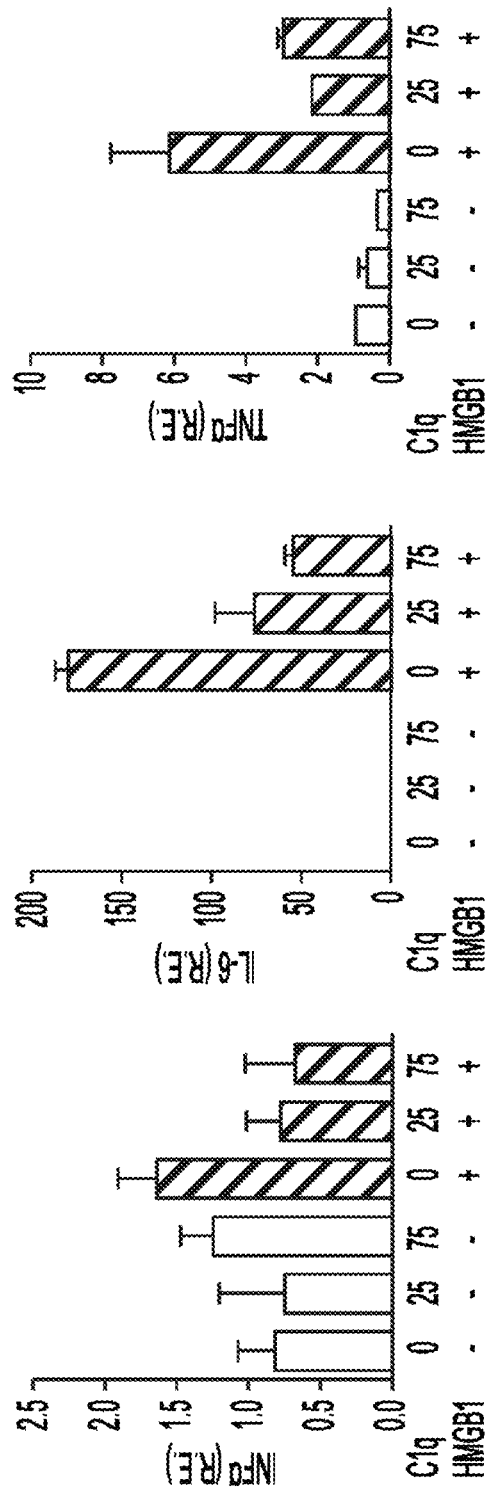
Figure 1G:
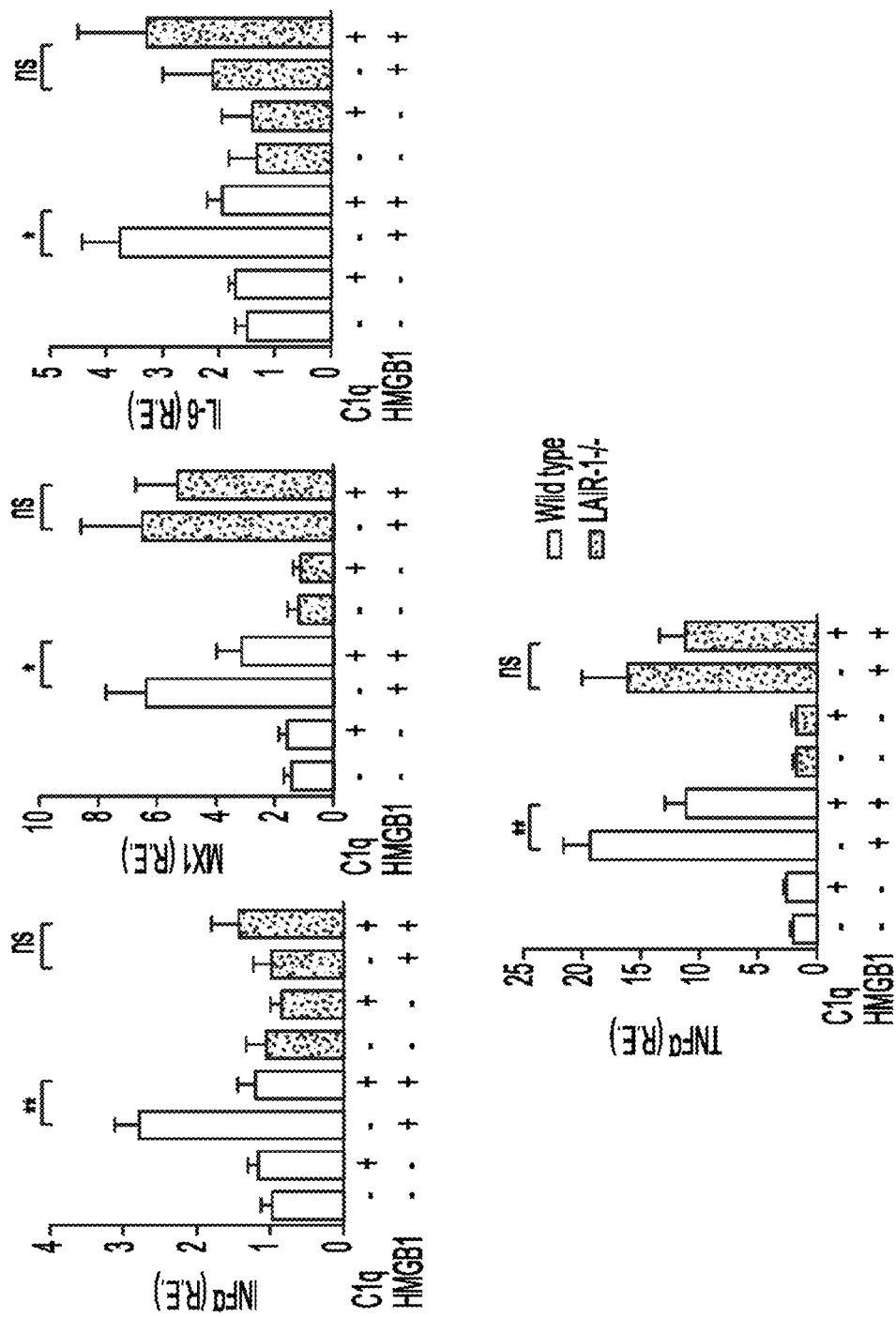

Next assessed was the involvement of LAIR-1 in this C1q-mediated inhibition of HMGB1-induced monocyte activation. Consistent with the notion that C1q inhibits the activity of HMGB1 by engaging LAIR-1, no effect was observed of C1q on HMGB1-mediated cytokine induction in monocytes treated with LAIR-1-specific siRNA (FIG. 1d). C1q failed to inhibit monocyte activation in the presence of soluble decoy receptor LAIR-2 (FIG. 1e). To study activation and inhibition of monocytes by HMGB1 and C1q, respectively, when monocytes are present in mixed cell populations, peripheral blood mononuclear cells (PBMCs) were incubated with HMGB1 and C1q and then the adherent cell population analyzed for cytokine induction. HMGB1 induced IFN, IL-6 and TNFα; C1q inhibited this HMGB1-mediated activation (FIG. 1f). This finding in a mixed cell population confirmed the previous observation in isolated monocytes. LAIR-1 deficient monocytes purified from spleens of mice expressing Lysozyme-Cre and harboring a floxed LAIR-1 gene also showed no inhibitory effect of C1q (FIG. 1g). Taken together, these results indicate that C1q can modulate immune homeostasis in blood by inhibiting HMGB1-induced monocyte activation through engaging LAIR-1.

C1q inhibits HMGB1 internalization: HMGB1 has an important role in potentiating the innate immune response to foreign (and endogenous) nucleic acids by transporting them into the cytoplasm of immune cells such as monocytes and DCs where they bind to endosomal TLRs. Since C1q inhibited HMGB1-induced cytokine secretion, it was asked whether this might result from a C1q-mediated inhibition of the internalization of HMGB1. FITC-labeled human HMGB1 was incubated with freshly isolated monocytes in the presence or absence of C1q and performed immunofluorescence microscopy. When the monocytes were maintained at 4° C., HMGB1 bound to surface receptors in the presence or absence of C1q (FIG. 2a). When monocytes were incubated at 37° C. in the absence of C1q, labeled HMGB1 accumulated in the cytoplasm. In contrast, cytosolic HMGB1 was significantly decreased in monocytes co-incubated with labeled HMGB1 and C1q. (FIGS. 2b and 2c). To test whether internalization of TLR ligands, which rely on HMGB1 for intracellular transport and trafficking, was also inhibited by C1q, the internalization of CpG oligonucleotides was assessed. FITC-labeled CpG oligonucleotides were internalized in the absence of C1q, but addition of C1q significantly reduced cellular internalization. C1q is known to block the effects of CpG (24), and the findings presented here provide a plausible molecular mechanism through which C1q accomplishes this previously described effect.

C1q's immunoregulatory function requires RAGE: It was previously reported that the internalization of HMGB1 requires HMGB1 binding to RAGE (25). Here it is investigated whether C1q was altering the interaction of HMGB1 with RAGE. As a first step toward probing the potential interactions between C1q, HMGB1 and RAGE, it was asked whether C1q could block HMGB1 activation in RAGE-deficient cells. To ensure a complete absence of RAGE, murine monocytes genetically deficient in RAGE (26) were used. Monocytes from the spleens of both wild type and RAGE-deficient mice were incubated with HMGB1 in the presence or absence of C1q. Consistent with previous studies (25), it was observed that RAGE-deficient monocytes failed to internalize HMGB1, with or without C1q (data not shown). HMGB1 did, however, induce cytokine expression in both wild type and RAGE-deficient monocytes (FIG. 3a), in agreement with previous reports that disulfide HMGB1 can signal through TLR4 and MD2 (26,27). As anticipated, co-incubation with C1q led to a reduction in HMGB1-induced proinflammatory cytokine gene transcription in wild type cells. In contrast, C1q mediated no change in HMGB1-induced gene transcription in RAGE-deficient cells (FIG. 3a), demonstrating that RAGE is required for C1q-mediated regulation of HMGB1.

To further probe the specificity of C1q-mediated monocyte inhibition, similar experiments were performed examining two TLR ligands, both of which can utilize HMGB1 as a cofactor: CpG and LPS. CpG mimics bacterial DNA and, through cytosolic TLR9 engagement in endosomes, leads to activation of MyD88 and downstream pathways (28). In contrast, LPS (endotoxin) is a component of the outer membrane of Gram-negative bacteria and, through cell surface TLR4 engagement, leads to activation of a proinflammatory cytokine cascade (29). Incubating these ligands with human monocytes, it was determined that while C1q inhibits CpG-mediated induction of pro-inflammatory cytokines (e.g., TNF) and IFN inducible genes (the IFN signature) (e.g., MX1), it has no effect on LPS-induced cytokine transcription. These striking findings suggest that C1q does not inhibit all monocyte activation; C1q inhibits HMGB1-mediated TLR9 but not HMGB1-mediated TLR4 signaling.

Figures 3A, 3B, 3C, 3D, 3E, 3F, 3G, 3H, 3I:
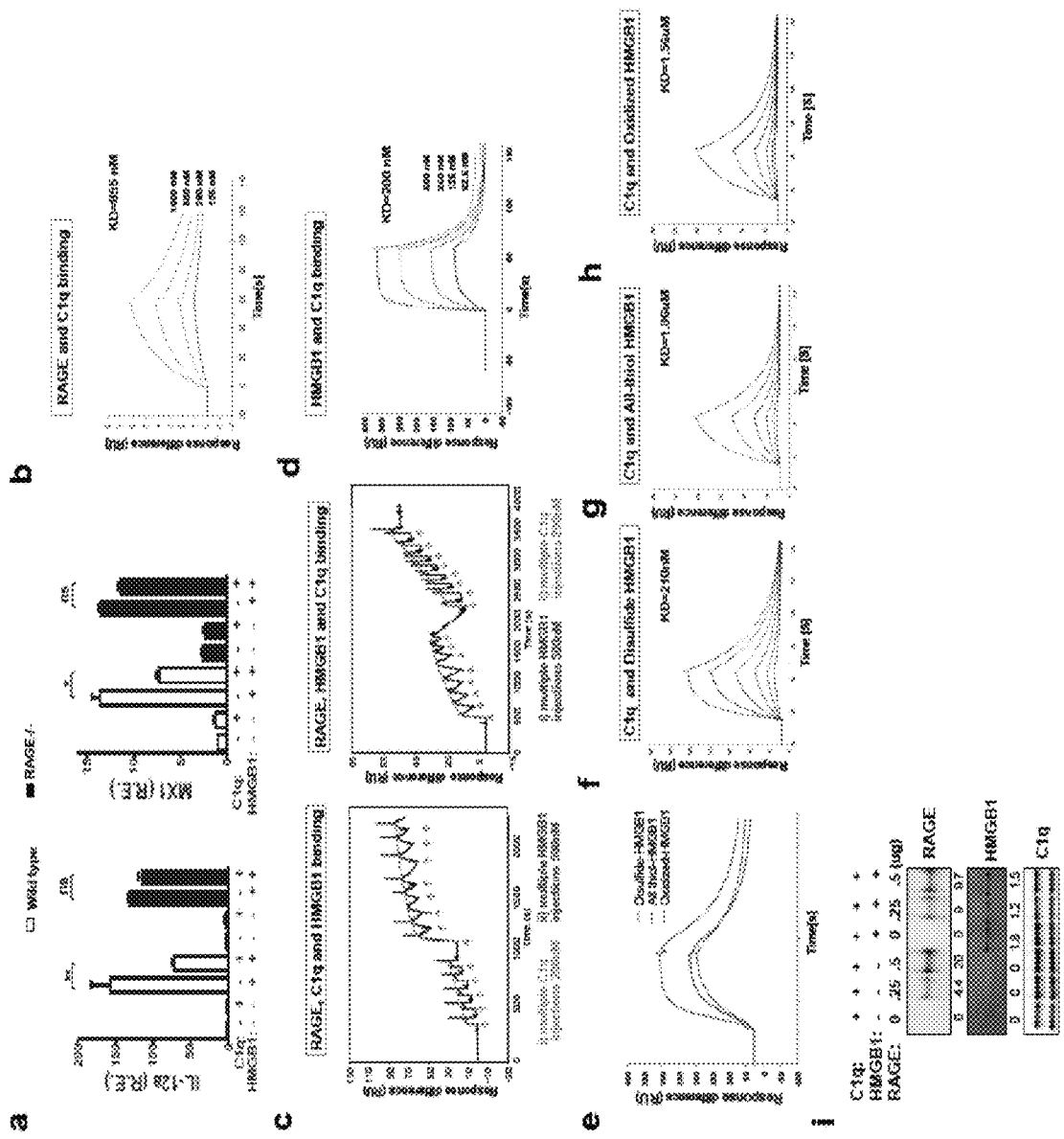

Since C1q inhibited the activation of RAGE by HMGB1 and since both C1q and HMGB1 have been shown to bind RAGE directly (30,31), it was determined if C1q prevented the interaction of HMGB1 with RAGE. For these experiments a surface plasmon resonance assay was employed and it was demonstrated that C1q binds RAGE in a dose-dependent manner (Kd=855 nM, FIG. 3b). No binding of the C1q collagen-like tail to RAGE was detected, confirming an interaction of RAGE with the globular head of C1q (data not shown). It was next asked whether C1q prevented an interaction of HMGB1 with RAGE, or whether a trimolecular complex of C1q, HMGB1 and RAGE could form. For this experiment, soluble RAGE (sRAGE) was immobilized on the sensor chip and C1q was introduced until the chip was saturated; then HMGB1 was added to form a sRAGE-C1q-HMGB1 complex (FIG. 3c, left). Since HMGB1 is significantly smaller than C1q, displacement of C1q by HMGB1 would have produced a lower signal after addition of HMGB1. This did not occur. Qualitatively similar results were observed when HMGB1 was added to immobilized sRAGE followed by C1q addition (FIG. 3c, right). In both cases C1q, HMGB1 and sRAGE formed a trimolecular complex. Interestingly, C1q also bound directly to HMGB1 in a concentration-dependent manner (Kd=200 nM, FIG. 3d), preferentially binding to the disulfide form of HMGB1, the form that functions as a cytokine (FIG. 3e-g). The existence of a trimolecular complex was confirmed by immobilizing C1q on beads, incubating with saturating amounts of HMGB1, followed by increasing concentrations of sRAGE (FIG. 3f). sRAGE was bound to C1q beads even in the presence of saturating amounts of HMGB1 (FIG. 3c). The data give evidence that C1q, RAGE and HMGB1 all interact.

C1q bridges RAGE and LAIR-1: It was previously demonstrated that C1q binds and activates the inhibitory receptor LAIR-1 (22) and it was shown above that this binding is critical to its inhibitory function. Since the C1q globular head binds RAGE while the C1q collagen tail binds LAIR-1, the next question was whether C1q might cross-link LAIR-1 to RAGE on the surface of monocytes. For these experiments we used a proximity ligation assay to investigate the localization of RAGE and LAIR-1 in the absence and presence of C1q. Polymerase-amplified fluorescence, indicative of RAGE-LAIR-1 binding, was only detected in the presence of C1q, with or without HMGB1 (FIG. 4a). This interaction is specific because probe control or isotype controls showed little or no signal and co-incubating C1q with LAIR-2 (a soluble decoy receptor) negated the cross-linking of RAGE and LAIR-1 (data not shown). Since C1q binds both RAGE and HMGB1 through its globular head, the fact that HMGB1 does not alter the C1q-mediated cross-linking of LAIR-1 and RAGE suggests that RAGE and HMGB1 bind C1q on different regions of the globular head. This agrees well with the surface plasmon resonance results which also demonstrate that HMGB1 and C1q bind different epitopes on RAGE. In the presence of HMGB1 and C1q, LAIR-1 migrated to lipid rafts where LAIR-1 colocalized with RAGE (FIG. 4b). Taken together, these results suggest that C1q can create a tetra-molecular complex of C1q, LAIR-1, HMGB1 and RAGE, bringing these molecules into the lipid raft with RAGE.

Figures 5A, 5B, 5C, 5D, 5E:
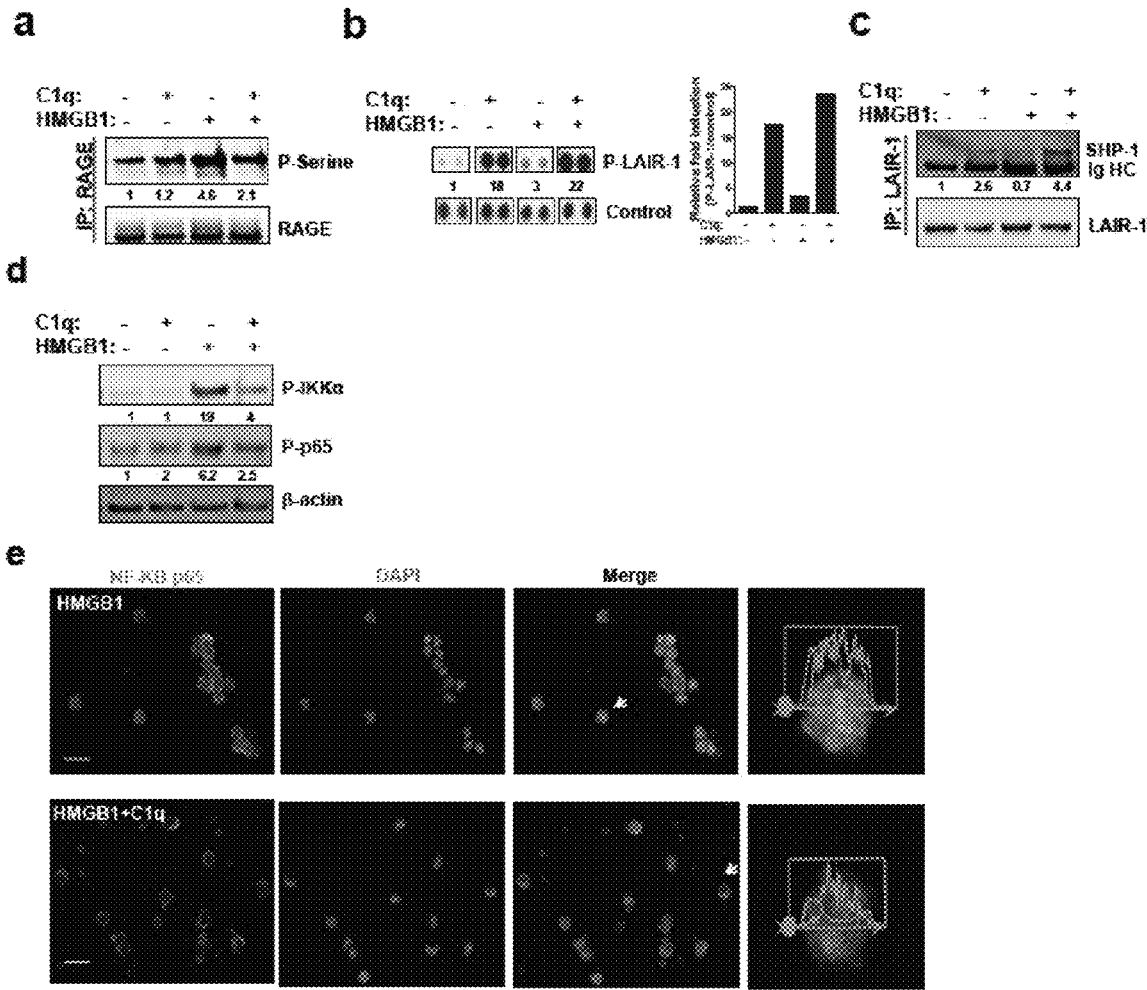

Phosphorylation of RAGE and LAIR-1 differs in the presence of HMGB1 and C1q In order to understand how the colocalization of RAGE and LAIR-1 might affect their downstream signaling pathways, the phosphorylation of several molecules was examined on primary human monocytes in the presence of HMGB1, C1q or both. A previous report that HMGB1 enhances phosphorylation of RAGE, which others have shown is mediated by PKC was confirmed (32), and it was demonstrated that the HMGB1-induced phosphorylation is diminished in the presence of C1q (FIG. 5a). It was also shown that C1q induces phosphorylation of LAIR-1 22, and observed that more SHP-1 is recruited to LAIR-1 when both HMGB1 and C1q are present (FIGS. 5b and c). Since phosphorylation on both ITIMs induces LAIR-1 to bind SHP-1, our data reveal that HMGB1 and C1q together enhance the phosphorylation of both ITIM motifs. Finally, C1q inhibited the downstream activation and nuclear translocation of NF-κB induced by HMGB1 (FIGS. 5d and e). Diminished HMGB1-induced phosphorylation of IKKα and diminished nuclear localization of p65 was observed in the presence of C1q. Together, these results indicate that in the presence of both C1q and HMGB1, RAGE is dephosphorylated, SHP-1 is recruited to LAIR-1, and NF-κB signaling pathway is inhibited.

Figures 6A, 6B, 6C, 6D, 6E:
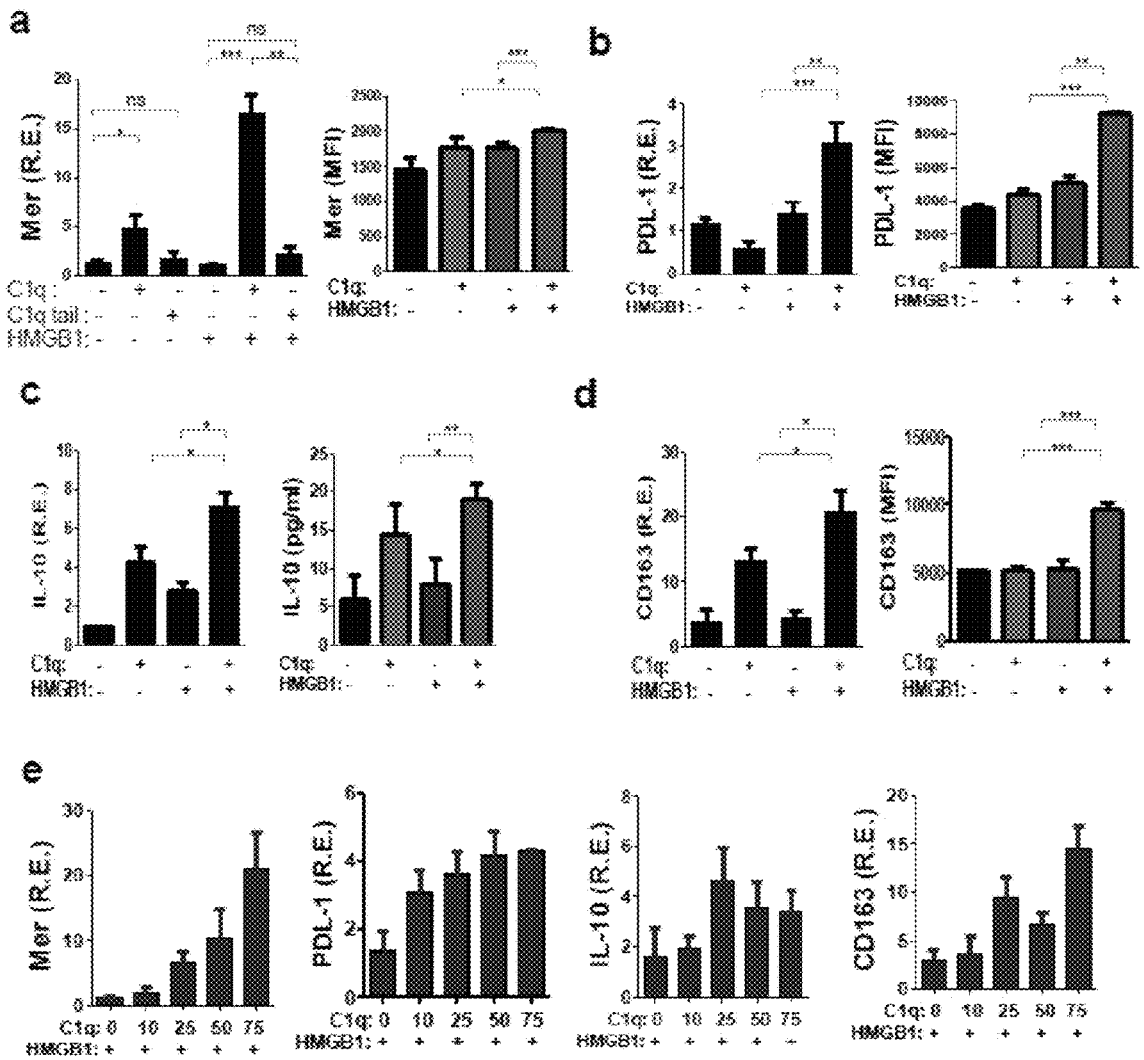

Monocytes exposed to both HMGB1 and C1q express a novel set of genes: To assess whether HMGB1 and C1q might further alter the activity of monocytes, primary human monocytes were assessed for expression of immunomodulatory proteins after incubation alone or in the presence of HMGB1, C1q or both for 24 h. Exposure to both HMGB1 and C1q induced the transcription and protein expression of a variety of anti-inflammatory factors, including Mer, a receptor tyrosine kinase important in the clearance of apoptotic debris, FIG. 6a); PDL-1, a molecule that suppresses T cell activation, FIG. 6b); transcription and secretion of IL-10, an anti-inflammatory cytokine (FIG. 6c); and transcription and expression of CD163, a marker of M2 macrophages (FIG. 6d). Physiologic levels of C1q were more potent than levels often observed in patients with SLE (25-50 µg/ml) (FIG. 6e). Importantly, exposure to HMGB1 and C1q tail did not mediate similar effects (FIG. 6a), confirming that C1q must interact with RAGE as well as LAIR-1 to induce M2 polarization and that coincident but uncoordinated signaling through RAGE and LAIR-1 is not sufficient. These findings indicate that when C1q cross-links LAIR-1 with RAGE and HMGB1 in lipid rafts it engages a program of monocyte differentiation into M2 macrophages.

Metabolic consequences of HMGB1 or HMGB1 and C1q exposure: The metabolic phenotype of immune cells has been previously shown to correlate with function. Classically activated (M1) macrophages have been shown to mainly utilize aerobic glycolysis for energy, while alternatively activated (M2) macrophages rely on fatty acid oxidative phosphorylation or gluconeogenesis (33). This shift toward aerobic glycolysis is coupled with transcriptional induction of glycolytic enzymes such as PKM2, or gluconeogenesis enzymes such as FBP1, and is thought to be important for cell survival in during oxidative stress (34,35). Importantly, aerobic glycolysis drives further HMGB1 secretion. HMGB1 has recently been shown to increase ATP production in a number of cell lines, including Jurkat and HL-60, owing to RAGE mediated signaling (12,36). It was investigated whether HMGB1 might promote aerobic glycolysis, and whether C1q could regulate this metabolic shift.

For these experiments, human monocytes were treated with buffer, HMGB1, C1q or HMGB1 with C1q for 24 hours and assessed the cellular bioenergetics by simultaneously measuring mitochondrial respiration and glycolysis using a SeaHorse XF analyzer. A more complete bioenergetic analysis was afforded by the sequential use of oligomycin (inhibits mitochondrial ATP synthase), FCCP (uncouples mitochondrial respiration from ATP synthesis) and rotenone plus antimycin A (blocks mitochondrial electron transport). While exposing monocytes to HMGB1 alone enhanced both baseline oxidative phosphorylation (as measured by oxygen consumption rate (OCR), FIG. 7a) and glycolytic metabolism (as measured by extracellular acidification rate (ECAR), FIG. 7b), the OCR/ECAR ratio was significantly decreased in HMGB1-exposed cells (FIG. 7c), demonstrating a shift to enhanced aerobic glycolysis, consistent with an M1 phenotype. In contrast, the inclusion of C1q together with HMGB1 prevented the alteration in cellular metabolism, presumably due to blockade of RAGE mediated signaling. This bioenergetic analysis, therefore, demonstrated that HMGB1-activated monocytes exhibited an M1 macrophage profile while HMGB1/C1q-treated monocytes exhibited an M2 macrophage profile 36, confirming the M1-like pro-inflammatory (HMGB1-mediated) vs. M2-like anti-inflammatory (HMGB1/C1q-mediated) gene expression patterns.

Monocyte differentiation to DCs is prevented by HMGB1 and C1q: As an early step toward an adaptive immune response, monocytes can differentiate into DCs and function in an antigen presenting role. In view of the M2-like state that C1q and HMGB1 elicited in monocytes, we wondered whether monocytes previously exposed to HMGB1 and C1q would lose their ability to differentiate into DCs. For these experiments, we induced monocyte differentiation to M2 macrophages followed by treatment with DC cytokines (GM-CSF and IL-4). Monocytes previously exposed to either C1q or HMGB1 and C1q for 24 hours retained expression of CD14 and LAIR-1, but expression was significantly higher in monocytes that had been exposed to both HMGB1 and C1q. In contrast, monocyte to DC differentiation occurred in previously untreated monocytes or monocytes previously treated with HMGB1 (FIG. 8a). These data suggest that exposure to HMGB1 and C1q drives monocytes into M2 macrophages that do not become antigen presenting cells in the presence of GM-CSF and IL-4. This was tested by using monocytes exposed to HMGB1, C1q or both in an allogeneic mixed lymphocyte reaction. Monocytes exposed to HMGB1 induced the strongest mixed lymphocyte reaction; monocytes exposed to both HMGB1 and C1q were poor stimulators of T cells (FIG. 8b).

HMGB1-linker-C1q peptide mimics C1q; cross-links RAGE and LAIR-1: An in situ proximal ligation assay was performed according to manufacturer's protocol (Duolink, Sigma). Following stimulation with C1q (122 nM) or HMGB1 A box-linker C1qa peptide (122 nM) for 15 min, human monocytes were washed three times with ice-cold PBS and were fixed with 4% (wt/vol) PFA for 1 hour at room temperature, seeded ($2\times10^5$ cells) on slides using cytospin (Shandon), permeablized with chilled MeOH for 4 min and with PBS/0.1% (vol/vol) Triton X-100 and blocked for 1 h at room temperature. Cells were then incubated overnight with a primary antibody pair directed to rabbit anti-RAGE (ab3611, Abcam) and to mouse anti-LAIR-1 (BD Bioscience), respectively. The cells were incubated with corresponding PLA probes conjugated to oligonucleotides (mouse MINUS and rabbit PLUS), then followed by ligation and rolling circle amplification in close proximity. Images were acquired using an AxioImage Z1 (Zeiss) apotome enabled (Zeiss) Fluorescent-intensity analysis of the images was performed using Zen2 (Zeiss). See FIG. 11.

TABLE 1

Function of fusion protein components.

| Name - function | Size | Description |
| --- | --- | --- |
| LAIR-1 binding - collagen | 12 aa | C1q A-chain (26-34) |
| RAGE binding - inhibition | 22 aa | HMGB1 A-Box (1-22) |
| RAGE binding - activation | 34 aa | HMGB1 B-Box (150-183) |
| $(Gly_4Ser)_3$ linker | 15 aa | successful use w/HMGB1 |

Confirmatory experiments were performed in vivo. RAGE and LAIR-1 cross-linking peptide ("RLCP") induced RvD2 and abolished LTB4 induction in murine macrophages by HMGB1 in vivo (FIG. 22). In addition, RLCP slowed the progression of serum anti-dsDNA antibodies in NZB/W mice in vivo (FIG. 23). RLCP also decreased anti-DNA IgM/IgG-producing splenocytes in NZB/W mice in vivo (FIG. 24). Finally, RLCP decreased inflammatory and increased anti-inflammatory markers in NZB/W splenocytes in vivo (FIG. 25) and, significantly, RLCP decreased kidney IgG deposition in NZB/W mice (photographic staining data not shown).

Discussion

It is well established that the healthy mammalian immune system is in a state of dynamic equilibrium, where activating stimuli are constantly balanced by negative feedback loops and inhibitory molecules in order to set a healthy homeostasis. Since autoreactive lymphoid cells have been shown to persist in healthy adults, and myeloid cells respond to molecular patterns that are endogenous (DAMPs) as well as those derived from pathogens (PAMPs), these regulatory mechanisms are of paramount importance in keeping a state of immune quiescence and avoiding unwanted autoimmunity. As an extracellular molecule, HMGB1 represents one of the evolutionarily ancient pro-inflammatory mediators comprising both chemokine and cytokine properties, depending on its redox state. As a cytokine, disulfide HMGB1 activates a program of inflammatory pathways that has been postulated to be essential for the production of anti-DNA antibodies in SLE (37). As a cytosolic molecule, it can regulate the threshold for autophagy and apoptosis, depending in part on its cellular localization (13,38,39). RAGE is a cellular receptor for HMGB1 and its expression determines the strength and duration of an immune response to HMGB1 and its cargo.

Like HMGB1, C1q is also evolutionarily ancient and has diverse functions. It can stimulate an antibody response, focusing antigen on follicular dendritic cells and decreasing the threshold for B cell activation (40,41). C1q can either activate or suppress the NLRP3 inflammasome (16). It has also been shown to suppress DC function, blocking monocyte to DC differentiation and DC production of inflammatory cytokines (22). It is a critical component of the process by which natural IgM antibodies mediate attenuation of DAMP- and/or PAMP-induced DC activation (42). It also plays a key role in the activation of intranasal antigen-induced tolerance, presumably because it predisposes DCs to the generation of Tregs (43). Recently, it was demonstrated that apoptotic cells bound by C1q suppress human macrophage and DC-mediated Th17 and Th1 cell activation (44); it appears that there are multiple pathways by which C1q can suppress adaptive immunity.

This study reveals previously unknown effects of HMGB1 and C1q on human monocyte activation and differentiation in inflammatory settings and in SLE. HMGB1 and C1q have opposing effects on human monocytes with HMGB1 inducing an M1-like phenotype. More surprisingly, their combined function results in the differentiation to a cell with the characteristics of M2 macrophages more favorable energetics, and which cannot differentiate into DCs. Thus these monocytes are effectively removed from forming the bridge to an adaptive immune response.

There are many receptors for both HMGB1 and C1q (3,15). Herein is disclosed a tetra-molecular interaction occurs between RAGE and LAIR-1 and their ligands of HMGB1 and C1q (FIG. 9). C1q cross-links LAIR-1 with RAGE and, in the presence of HMGB1, induces co-localization of these receptors to lipid rafts, inhibiting RAGE activity as evidenced by reduced RAGE phosphorylation. As phosphorylated RAGE is a major transporter of HMGB1 and its cargo into the cytosol, internalization of HMGB1 is significantly inhibited in the presence of C1q. Although C1q alone can bind LAIR-1 on monocytes, and lead to its phosphorylation, presumably by Hck, a more suppressive role of C1q depends on co-stimulation with HMGB1 leading to enhanced recruitment of SHP-1. Our model suggests a multi-modal function of C1q. In the absence of inflammatory stimuli, C1q represses the inflammatory properties of the low levels of HMGB1 normally present in human serum (FIG. 9b). In the presence of higher levels of HMGB1, however, C1q acts as a molecular switch that drives monocyte differentiation to an immunosuppressive M2-like cell type (FIG. 9c). Finally, when HMGB1 levels are too high, C1q fails to dampen monocyte differentiation to M1 like macrophages (FIG. 9a).

The cooperation of HMGB1 with C1q in the inflammatory setting may terminate inflammation through inducing M2 macrophage differentiation with expression of suppressive molecules such as Mer, PDL-1 and IL-10 (45). Moreover, HMGB1- and C1q-exposed monocytes cannot differentiate into dendritic cells and cannot participate in supporting a mixed lymphocyte reaction. This suggests that HMGB1 together with C1q would limit monocyte function as APCs in an adaptive immune response.

It is well established that SLE pathology begins after class switching of autoantibodies from IgM to IgG and, further, that IgM autoantibodies can protect against disease onset (46). This model explains how IgM immune complexes are suppressive of innate inflammation while IgG immune complexes provoke an inflammatory response, IgM complexes engage C1q and LAIR-1, while IgG complexes directly engage Fc receptors. Interestingly, it has been reported (37) that immunoglobulin class switching to IgG can be facilitated through engagement of HMGB1 to TLR2. Whether C1q can alter this activity of HMGB1 is not known.

These findings emphasize the importance of generating therapeutic approaches to selectively engage RAGE and LAIR-1 to target DAMP-mediated inflammation while preserving other protective immune responses, such as the response to LPS. FIGS. 22-25 demonstrate the practicality of this in vivo.

In blood, circulating C1q engages LAIR-1 and maintains quiescence of monocytes. When increased levels of HMGB1 are present as a consequence of tissue damage or infection, these cells may differentiate toward macrophages or DCs and migrate to where C1q can be actively secreted by myeloid cells to dampen immune activation. Indeed, we hypothesize that infiltrating monocytes/M2 macrophages engage in resolution of inflammation while tissue-resident myeloid cells may not as they experience LAIR-1 activation through extracellular matrix collagen which fails to cross-link LAIR-1 to RAGE, and so will not lead to M2 like differentiation. It is interesting to consider whether RAGE also binds to other C1q binding partners beyond HMGB1, such as S100 proteins and amyloid β, which are generated during inflammation (47,48). Consistent with this hypothesis, dysregulation of C1q has been associated with the development of various inflammatory diseases including rheumatoid arthritis, Alzheimer's disease as well as SLE.

Taken together, the data demonstrate a mechanism by which C1q regulates the inflammatory properties of HMGB1. Since C1q is produced in sites of inflammation, and considering the overwhelming proportion of C1q deficient patients who manifest with an autoimmune disease, this immune-regulatory mechanism of C1q is evidently of great importance in safeguarding an appropriately regulated immune response. Moreover, the fact that motifs within C1q and HMGB1 can activate an unappreciated natural program of immune quiescence raises the exciting possibility of harnessing this pathway to develop novel mechanism-based lupus therapeutics.

Furthermore, since DWEYS peptide additionally prevents internalization of HMGB1 also, and binds RAGE, blocking HMGB1 from binding to RAGE, a fusion protein comprising DWEYS and C1q will also be advantageous to administer in certain autoimmune inflammatory conditions, such as SLE or RA. In keeping myeloid cells activated and/or crosslinking and preventing internalization, therapeutic effects are expected.

Methods

Reagents: C1q purified from pooled normal human sera was obtained from Complement Technology. C1q tail was purified from whole C1q as previous described (22). Recombinant HMGB1 (Calmodulin Binding Protein Epitope, Cbp tagged), reduced or oxidized forms HMGB1 and monoclonal anti-HMGB1 antibody (2G7) were generated as previously described (49). Human recombinant (hr) LAIR-2 and hrRAGE were purchased from R&D Systems. CpG ODN 2216, FITC-CpG ODN 2216 and ultra pure LPS were purchased from Invivogen. FITC was conjugated to HMGB1 using amine-reactive probes (Invitrogen) per the manufacturer's protocol. Biotin labeling of C1q was performed using an EZ-Link Sulfo-NHS-LC Biotinylation kit (Thermo Scientific) per the manufacturer's instructions. SpeedBeads™ streptavidin microparticles were purchased from Thermo Scientific. Fluorochrome-conjugated and unconjugated antibodies were purchased: PE-labeled or unlabeled mouse anti-human LAIR-1 (DX26, BD Bioscience); goat anti-human LAIR-1 (T-15), mouse anti-SHP-1 (D-11), goat anti-calmodulin binding protein tag (Santa Cruz Biotechnology); rabbit anti-RAGE, rabbit anti-flotillin, rabbit anti-NFκB p65 (Abcam); mouse anti-phospho-IKKα, rabbit anti-phospho-Serine, rabbit anti-RAGE and rabbit anti-phospho-p65 (Cell Signaling); mouse anti-0 actin (AC-15, Sigma); mouse anti-C1q (Quidel); FITC-anti-Mer, Pacific Blue-anti-CD11b, APC-anti-CD11c, APC-Cy7-anti-CD14, Pacific Blue-CD16, PE-anti-CD163, PECy7-anti-PDL-1, anti-CD3 (OKT3), FITC-anti-CD4, HRP-anti-goat IgG and isotype-matched control antibodies (eBioscience); Alexa Fluor 594-conjugated anti-rabbit IgG and Cell Trace Violet (Life Technologies); 1×RIPA cell lysis buffer (Invitrogen); protease inhibitor cocktail, phosphatase inhibitors (Pierce, Waltham, MA); PBS/4% paraformaldehyde (PFA), Triton X-100, Tween-20 and NP-40 (Sigma). Purified proteins and culture reagents were endotoxin tested (<0.1 EU/ml) either by the manufacturer using a Limulus Amebocyte Lysate (LAL) assay kit performed per the manufacturer's instructions (Endosafe).

Monocyte isolation and stimulation: Human PBMCs were obtained following institutional guidelines of the Feinstein Institute for Medical Research (Feinstein) and isolated from blood of healthy donors by density centrifugation (New York Blood Bank). Monocytes were negatively enriched using a human monocyte enrichment kit (Stem Cell Technology). Purity of monocytes (≥90% CD11b+CD14+LAIR-1+) was determined by flow cytometry. Purified monocytes ($2\times10^6$ cells/ml) were cultured in U-bottom 96-well plate and stimulated with HMGB1 (3 or 10 μg ml-1), CpG 2216 (5 uM), LPS (0.1-10 μg/ml), hrLAIR-2 (20 μg/ml) or C1q (25 μg ml-1) in X-Vivo 15 serum free medium (Lonza), and harvested at the indicated time points. For FIG. 1f, PBMCs (2×106 cells/ml) were incubated in a flat-bottom 96-well plate with HMGB1 (3 μg/ml) and/or C1q (25 μg/ml) for 6 h, and adherent cells were harvested. In order to differentiate into DCs, monocytes were pre-incubated with C1q and HMGB1 alone or together for 24 h, extensively washed and further cultured for 2 days in the presence of 50 ng ml-1 GM-CSF and 20 ng/ml IL-4 (R&D). Splenic murine monocytes from wild type mice, RAGE deficient or LAIR-1 conditional knockout mice were isolated using EasySep mouse monocyte enrichment kit (Stem Cell Technology). C57BL/6 mice, Lysozyme2-Cre transgenic mice were purchased from Jackson Laboratory. Myeloid specific LAIR-1 conditional knockout mice (Lysozyme2-Cre×LAIR fl/fl) were bred and maintained in our facility (Feinstein) under specific pathogen-free conditions. RAGE deficient mice (Department of Medicine, Karolinska Institute Stockholm, Sweden) were maintained at Feinstein. Eight-to ten weeks old male mice were used for experiments. All animal procedures were approved by the Feinstein Institutional Animal Care and Use Committee.

RT-PCR analysis and primers: Total RNA was extracted from cells ($1-2\times10^6$ cells per sample) with an RNeasy kit (Qiagen, Venlo, Limburg, Netherlands) and cDNA was generated using an iScript cDNA synthesis kit (Bio-Rad laboratories). Real Time-PCR was performed on a Light Cycler 480 II (Roche) using Light Cycler 480 master mix with primers (Applied Biosystems) for IFNα1 (Hs00256882), IFNα7 (mm02525960), MX1 (Hs00182073, mm01217998), IL-6 (Hs00985639, mm99999064), TNFα (Hs00174128, mm00443258), IL-12a (Hs00168405), Mer (Hs01031973), PDL-1 (Hs01125301), IL-10 (Hs00961622), CD163 (Hs00174705), HPRT1 (Hs99999909, mm01545399) and Polr2a (Hs00172187). The genes of interest were normalized to the expression of house keeping genes and were compared to a control condition with no treatment. The relative induction was calculated by 2-ΔΔCt.

Transfection: For RNA interference assays, human monocytes were transfected using an Amaxa Nucleofector kit (Lonza) with a greater than 40% transfection efficiency. siRNAs were obtained from Qiagen. The target sequence of human LAIR1-11 is CAGCATCCAGA AGGTTCGTTA (SEQ ID NO:9). The efficiency of knockdown was determined by flow cytometry and q-PCR.

Cytokine analysis: Cytokine levels were measured using a Human Proinflammatory 7-plex assay following the manufacturer's protocols (Meso Scale Discovery (MSD). MSD plates were analyzed on the MS2400 imager (MSD). All standards and samples were run in duplicates.

Immunofluorescence Microscopy: In situ proximal ligation assay was performed according to manufacturer's protocol (Duolink, Sigma). Following stimulation, human monocytes were washed three times with ice-cold PBS and were fixed with 4% (wt/vol) PFA for 1 hour at room temperature, seeded ($2\times10^5$ cells) on slides using cytospin (Shandon), permeablized with chilled MeOH for 4 min and with PBS/0.1% (vol/vol) Triton X-100 and blocked for 1 h at room temperature. Cells were then incubated overnight with a primary antibody pair directed to rabbit anti-RAGE (ab3611, Abcam) and to mouse anti-LAIR-1 (BD Bioscience), respectively. The cells were incubated with corresponding PLA probes conjugated to oligonucleotides (mouse MINUS and rabbit PLUS), then followed by ligation and rolling circle amplification in close proximity. Images were acquired using AxioVision software and a confocal microscope (Olympus). Quantification was performed using Zen2 (Zeiss). For HMGB1 or CpG internalization assays, isolated human monocytes were washed with PBS and stimulated by FITC-labeled HMGB1 or CpG ODN 2216 with or without C1q for 15 min at 4° C. or 37° C. Cells were washed three times with cold-PBS and fixed with 4% PFA and stained with PECy5-anti-human CD14 antibody (BD biosciences) or propidium iodide (PI). Before image acquisition, cells were displayed on slides using cytospin (Shandon) and mounted using Dako mounting medium (Agilnet technologies) or 4,6-diamidino-2-phenylinole (DAPI) containing mounting medium (Sigma). PI or DAPI was used for nuclear staining. To analyze nuclear translocation of NFκB p65, cells were stimulated with HMGB1 or HMGB1 plus C1q for 1 h at 37° C., fixed and permeabilized with PBS/ 0.5% (vol/vol) Triton-X-100 for 10 min, washed, blocked with 2% (wt/vol) BSA and 2% (vol/vol) goat serum (Life Technologies) for 30 min at room temperature before incubation with anti-rabbit NFκB p65 (Abcam) at 4° C. overnight. After washing, cells were stained with Alexa Fluor 594 anti-rabbit IgG (Life Technologies), and mounted DAPI-containing medium. Images were acquired using an AxioImage Z1 (Zeiss) apotome enabled (Zeiss) Fluorescent-intensity analysis of the images was performed using Zen2 (Zeiss).

Surface Plasmon Resonance analysis (SPR): For real-time binding interaction studies, a BIAcore T200 instrument (GE Healthcare) was used. For RAGE and C1q, HMGB1 and C1q binding analyses, C1q (50 µg/ml) or HMGB1 (5 µ/ml) were immobilized on a CMS series chip (GE Healthcare). A 1:1 mixture of N-hydroxysuccinimide and N-ethyl-N-(dimethyaminopropyl) carbodiimide was used to activate 2 flow-cells of the CMS chip. One flow-cell was used as a reference and thus immediately blocked upon activation by 1 M ethanolamine. The sample flow-cell was injected with the diluted C1q or HMGB1 were injected at a flow rate of 10 µl min-1. The C1q injection was stopped when the surface plasmon resonance reached 2000 response difference (RU); the HMGB1 injection was stopped at ~60-100 RU. The analytes (RAGE or C1q) were introduced to the immobilized C1q or HMGB1 at 5 different concentrations. The analytes were diluted in 1×PBS+0.01% (vol/vol) tween-20 buffer. The analytes were sequentially injected at a flow rate of 30 µl/min for 60 s at 25° C. The KD was dertermined using the BIAcore evaluation software 2.0 (GE Healthcare) supposing a 1:1 binding ratio.

For the RAGE, C1q and HMGB1 complex formation assay, RAGE (20 µg/ml) was immobilized on a CMS chip. The first analyte (C1q fixed at 200 nM) was introduced to the immobilized sRAGE in multiple times until the chip was saturated, and then the second analyte (HMGB1 fixed at 500 nM) was injected to the RAGE-C1q complex in multiple times. The dissociation time was set for 1 minute. RAGE, HMGB1 and C1q complex formation assay was performed by a similar procedure.

For the SPR binding assay of different redox states of HMGB1 and C1q, high-level immobilization of C1q was immobilized onto a CMS chip (GE Healthcare). The C1q protein was diluted to a concentration of 20 µg/ml in 10 mM Acetate buffer (pH=4.5). A 1:1 mixture of N-hyrdoxysuccinimide and N-ethyl-N-(dimethylaminopropyl) carbodiimide was used to activate 2 flow-cells of the CMS chip. One flow-cell was used as a reference and thus immediately blocked upon activation by 1 M ethanolamine (pH=8.5). The sample flow-cell was injected with the diluted C1q at a flow rate of 10 µl/min. The C1q injection was stopped when the surface Plasmon resonance reached 2200 RU. The analyte (HMGB1) was diluted in 1×HBS-N+0.05% tween-20 buffer (filtered—0.22 um). Three redox states of HMGB1 were sequentially injected at a flow rate of 20 µl/min for 60 s at 25° C., the dissociation time was set for 3 minutes. The concentration was set at 500 nM.

For, Kinetics assay of different redox states of HMGB1 and C1q, the analytes (Disulfide-HMGB1, all thiol-HMGB1, Oxidized-HMGB1) were introduced to the immobilized C1q at 6 different concentrations. The analytes were diluted in 1×HBS-N+0.05% tween-20 buffer (filtered—0.22 um). The analytes were sequentially injected at a flow rate of 20 µl/min for 60 s at 25° C. The dissociation time was set for 3 minutes. The KD for each analyte was determined using the Biacore evaluation software 2.0 supposing a 1:1 binding ratio.

Trimolecular complex assay: Biotinylated-C1q (20 µg/ml) was precoated to SpeedBeads™ (Streptavidin-conjugated microbeads, Thermo Scientific). Beads were saturated with HMGB1, then incubated with RAGE. After extensive washing, RAGE, HMGB1 and C1q were visualized by SDS-PAGE and Western blot.

Lipid raft fractionation: Lipid rafts were prepared as described (50). Monocytes ($5 \times 10^6$) were lysed in 1 ml THE buffer (25 mM Tris, 150 mM NaCl, 5 mM EDTA) containing 1% Triton and incubated for 30 min on ice. Lysates were homogenized with 10 strokes of a dounce homogenizer, mixed with 2 ml of 80% sucrose in TNE buffer, and transferred to a centrifuge tube. Samples were overlaid with 4 ml of 30% sucrose and 2 ml of 5% sucrose in TNE. After centrifugation for 16 h at 180,000 g in a Beckman Coulter SW41Ti rotor, 0.8 ml fractions were collected from the top of the gradient. Each fraction was subjected to slot blot analysis to identify GM1-enriched rafts fraction using FITC-conjugated cholera toxin-B subunit (Sigma). Lipid raft fractions were precipitated with TCA and washed with 70% EtOH, then subjected to slot blot analysis or Western blot.

Immunoprecipitation and Western blot. Total protein extracts were prepared as described (22). Monocytes (2-5× 106 cells/ml) were washed in ice-cold PBS and lysed in 1×RIPA buffer containing complete protease inhibitor mixture (Roche) and phosphatase inhibitor (Pierce) for 1 h on ice. For immunoprecipitation, anti-LAIR-1 antibody (BD Bioscience) or anti-RAGE antibody (Abcam) was incubated with the lysate overnight at 4° C. prior to being incubated with protein G-dynabeads (Life Technologies). Proteins were then separated by SDS-PAGE, transferred to nitrocellulose or PVDF membranes, and immunoblotted with appropriate antibodies. Bands were detected using the ECL reagent (Thermo Scientific) or using the Odyssey Infrared Imaging system (LI-COR) to detect secondary antibodies conjugated with Infrared 680 or 800.

Phospho-immunoreceptor array: Tyrosine phosphorylated LAIR-1 was determined by human phosphoimmunoreceptor array (Proteome Profiler Array; R&D systems) according to the manufacturer's protocol and as described (22). Phosphorylation levels of individual analytes were determined by average pixel density of duplicate spots; values were obtained after subtraction of background and were normalized to positive control spots.

Flow cytometry: Cells were suspended in staining buffer containing 2% BSA and incubated with Fc block (Miltenyi Biotec) for 15 min on ice. The cells were then incubated with experimental or isotype matched antibodies and washed. Events were acquired using either an LSRII or Fortessa cell analyzer (BD Biosciences), and data were analyzed using FlowJo (Tree star).

Cell metabolism analysis using SeaHorse Cellular Flux assay. Monocytes ($300 \times 10^3$ cell/well) from healthy donors were isolated as previously described, seeded in triplicates on SeaHorse XfP plates in X-Vivo 15 culture medium, and treated with HMGB1 (3 µg/ml) with or without C1q (25 µg ml-1), or maintained in culture medium alone (untreated control) for 24 h. One hour prior to measurement, culture medium was exchanged for assay medium (unbuffered DMEM (Sigma), supplemented with 10 mM Glucose, 1 mM Pyruvate and 2 mM Glutamine for mitochondrial assays, or with 2 mM Glutamine alone for glycolytic assays. Reagents were injected during the measurement to achieve final concentrations of oligomycin (1 µM), carbonyl cyanide p-(trifluoromethoxy) phenylhydrazone (FCCP) (1 nM), Rotenone/antimycin A (0.5 µM). Glucose (10 mM), and 2-Deoxy-D glucose (50 mM). Oxygen consumption rate (OCR) and Extracellular acidification rate (ECAR) values were measured using a SeaHorse XfP instrument (SeaHorse bioscience). Measured values were normalized to the number of live cells present in each well as determined by a trypan blue staining by the end of each run. For OCR/ECAR ratio calculations, an average of the last two basal readings was used for both OCR and ECAR.

Mixed-lymphocyte reaction: Monocytes ($1 \times 10^5$ cells per well) were plated on flat-bottom 96 well plates and incubated with or without HMGB1 (3 μg/ml) or C1q (25 μg/ml) in X-Vivo 15 medium for 24 h, washed then cultured further 2 more days. Allogeneic CD4 T lymphocytes were isolated from blood using the Naïve CD4+ T cell isolation kit II (Miltenyi Biotec.) following the manufacturer's protocol. Cells were analyzed by flow cytometry (>90%). T cells were labeled with 5 μM Cell Trace Violet cell proliferation kit (Thermo Fisher Scientific), added to mono/macrophages at a density of $2 \times 10^5$ cells/well (a 1:2 ratio) in the presence of 1 μg/ml anti-CD3 (OKT3, eBioscience). Control cultures contained medium only or T cells or mono/macrophages alone. After 4 days, cells were stained with FITC-anti-CD4, PerCPCy 5.5-CD14, PE-LAIR-1 and fixable viability dyes (FVD, eBioscience) for 20 min at room temperature and subsequently washed and fixed. Live cells (FVD-negative cells) were then gated on CD4-positive, and cell trace violet was assessed by flow cytometry on a BD LSR II (BD Biosciences). Cell proliferation was analyzed as described (51). The % divided cells was defined as the probability that a cell has divided at least once from the original population. The division index was defined as the average number of cell divisions that a cell in the original population has undergone.

Statistical analysis: Student's t-test, one-way ANOVA and Kruskal-Wallis were used for statistical analyses with Prism 6.0 (Graphpad, La Jolla, CA) or SPSS 16 (IBM). Adjusted P values (Bonferoni/Dunn) of less than 0.05 were considered significant.

REFERENCES

1. Ronnblom, L. & Elkon, K. B. Cytokines as therapeutic targets in SLE. *Nat Rev Rheumatol* 6, 339-347 (2010).
2. Mohan, C. & Putterman, C. Genetics and pathogenesis of systemic lupus erythematosus and lupus nephritis. *Nature reviews. Nephrology* 11, 329-341 (2015).
3. Andersson, U. & Tracey, K. J. HMGB1 is a therapeutic target for sterile inflammation and infection. *Annual review of immunology* 29, 139-162 (2011).
4. Harris, H. E., Andersson, U. & Pisetsky, D. S. HMGB1: a multifunctional alarmin driving autoimmune and inflammatory disease. *Nat Rev Rheumatol* 8, 195-202 (2012).
5. Scaffidi, P., Misteli, T. & Bianchi, M. E. Release of chromatin protein HMGB1 by necrotic cells triggers inflammation. *Nature* 418, 191-195 (2002).
6. Yanai, H. et al. HMGB proteins function as universal sentinels for nucleic-acid-mediated innate immune responses. *Nature* 462, 99-103 (2009).
7. Sirois, C. M. et al. RAGE is a nucleic acid receptor that promotes inflammatory responses to DNA. *J Exp Med* 210, 2447-2463 (2013).
8. Tian, J. et al. Toll-like receptor 9-dependent activation by DNA-containing immune complexes is mediated by HMGB1 and RAGE. *Nat Immunol* 8, 487-496 (2007).
9. Huebener, P. et al. The HMGB1/RAGE axis triggers neutrophil-mediated injury amplification following necrosis. *J Clin Invest* 125, 539-550 (2015).
10. Popovic, P. J. et al. High mobility group B1 protein suppresses the human plasmacytoid dendritic cell response to TLR9 agonists. *J Immunol* 177, 8701-8707 (2006).
11. Aikawa, E., Fujita, R., Kikuchi, Y., Kaneda, Y. & Tamai, K. Systemic high-mobility group box 1 administration suppresses skin inflammation by inducing an accumulation of PDGFRalpha(+) mesenchymal cells from bone marrow. *Sci Rep* 5, 11008 (2015).
12. Kang, R. et al. The HMGB1/RAGE inflammatory pathway promotes pancreatic tumor growth by regulating mitochondrial bioenergetics. *Oncogene* 33, 567-577 (2014).
13. Tang, D. et al. High-mobility group box 1 is essential for mitochondrial quality control. *Cell metabolism* 13, 701-711 (2011).
14. Yang, H. et al. MD-2 is required for disulfide HMGB1-dependent TLR4 signaling. *J Exp Med* 212, 5-14 (2015).
15. Kouser, L. et al. Emerging and Novel Functions of Complement Protein C1q. *Frontiers in immunology* 6, 317 (2015).
16. Benoit, M. E., Clarke, E. V., Morgado, P., Fraser, D. A. & Tenner, A. J. Complement protein C1q directs macrophage polarization and limits inflammasome activity during the uptake of apoptotic cells. *J Immunol* 188, 5682-5693 (2012).
17. Elkon, K. B. & Santer, D. M. Complement, interferon and lupus. *Curr Opin Immunol* 24, 665-670 (2012).
18. Galvan, M. D., Greenlee-Wacker, M. C. & Bohlson, S. S. C1q and phagocytosis: the perfect complement to a good meal. *J Leukoc Biol* 92, 489-497 (2012).
19. Botto, M. & Walport, M. J. C1q, autoimmunity and apoptosis. *Immunobiology* 205, 395-406 (2002).
20. Kirschfink, M. et al. Complete functional C1q deficiency associated with systemic lupus erythematosus (SLE). *Clin Exp Immunol* 94, 267-272 (1993).
21. Botto, M. et al. Homozygous C1q deficiency causes glomerulonephritis associated with multiple apoptotic bodies. *Nat Genet* 19, 56-59 (1998).
22. Son, M., Santiago-Schwarz, F., Al-Abed, Y. & Diamond, B. C1q limits dendritic cell differentiation and activation by engaging LAIR-1. *Proc Natl Acad Sci USA* 109, E3160-3167 (2012).
23. Andersson, U. et al. High mobility group 1 protein (HMG-1) stimulates proinflammatory cytokine synthesis in human monocytes. *J Exp Med* 192, 565-570 (2000).
24. Son, M. & Diamond, B. C1q-mediated repression of human monocytes is regulated by leukocyte-associated Ig-like receptor 1 (LAIR-1). *Mol Med* 20, 559-568 (2014).
25. Xu, J. et al. Macrophage endocytosis of high-mobility group box 1 triggers pyroptosis. *Cell Death Differ* 21, 1229-1239 (2014).
26. Yang, H. et al. A critical cysteine is required for HMGB1 binding to Toll-like receptor 4 and activation of macrophage cytokine release. *Proc Natl Acad Sci USA* 107, 11942-11947 (2010).
27. Liliensiek, B. et al. Receptor for advanced glycation end products (RAGE) regulates sepsis but not the adaptive immune response. *J Clin Invest* 113, 1641-1650 (2004).
28. Chuang, T. H., Lee, J., Kline, L., Mathison, J. C. & Ulevitch, R. J. Toll-like receptor 9 mediates CpG-DNA signaling. *J Leukoc Biol* 71, 538-544 (2002).
29. Lu, Y. C., Yeh, W. C. & Ohashi, P. S. LPS/TLR4 signal transduction pathway. *Cytokine* 42, 145-151 (2008).
30. Ma, W. et al. RAGE binds C1q and enhances C1q-mediated phagocytosis. *Cell Immunol* 274, 72-82 (2012).
31. Hori, O. et al. The receptor for advanced glycation end products (RAGE) is a cellular binding site for amphoterin. Mediation of neurite outgrowth and co-expression of rage 32. Sakaguchi, M. et al. TIRAP, an adaptor protein for TLR2/4, transduces a signal from RAGE phosphorylated upon ligand binding. *PloS one* 6, e23132 (2011).
33. Kelly, B. & O'Neill, L. A. Metabolic reprogramming in macrophages and dendritic cells in innate immunity. *Cell Res* 25, 771-784 (2015).
34. Yang, L. et al. PKM2 regulates the Warburg effect and promotes HMGB1 release in sepsis. *Nat Commun* 5, 4436 (2014).
35. Reales-Calderon, J. A., Aguilera-Montilla, N., Corbi, A. L., Molero, G. & Gil, C. Proteomic characterization of human proinflammatory M1 and anti-inflammatory M2 macrophages and their response to *Candida albicans*. *Proteomics* 14, 1503-1518 (2014).
36. Izquierdo, E. et al. Reshaping of Human Macrophage Polarization through Modulation of Glucose Catabolic Pathways. *J Immunol* 195, 2442-2451 (2015).
37. Wen, Z. et al. Autoantibody induction by DNA-containing immune complexes requires HMGB1 with the TLR2/microRNA-155 pathway. *J Immunol* 190, 5411-5422 (2013).
38. Zhu, X. et al. Cytosolic HMGB1 controls the cellular autophagy/apoptosis checkpoint during inflammation. *J Clin Invest* 125, 1098-1110 (2015).
39. Liu, L. et al. HMGB1-DNA complex-induced autophagy limits AIM2 inflammasome activation through RAGE. *Biochem Biophys Res Commun* 450, 851-856 (2014).
40. Cutler, A. J. et al. T cell-dependent immune response in C1q-deficient mice: defective interferon gamma production by antigen-specific T cells. *J Exp Med* 187, 1789-1797 (1998).
41. Kolev, M., Le Friec, G. & Kemper, C. Complement—tapping into new sites and effector systems. *Nat Rev Immunol* 14, 811-820 (2014).
42. Chen, Y., Park, Y. B., Patel, E. & Silverman, G. J. IgM antibodies to apoptosis-associated determinants recruit C1q and enhance dendritic cell phagocytosis of apoptotic cells. *J Immunol* 182, 6031-6043 (2009).
43. Fossati-Jimack, L. et al. Intranasal peptide-induced tolerance and linked suppression: consequences of complement deficiency. *Immunology* 144, 149-157 (2015).
44. Clarke, E. V., Weist, B. M., Walsh, C. M. & Tenner, A. J. Complement protein C1q bound to apoptotic cells suppresses human macrophage and dendritic cell-mediated Th17 and Th1 T cell subset proliferation. *J Leukoc Biol* 97, 147-160 (2015).
45. Manicassamy, S. & Pulendran, B. Dendritic cell control of tolerogenic responses. *Immunol Rev* 241, 206-227 (2011).
46. Gronwall, C. et al. IgM autoantibodies to distinct apoptosis-associated antigens correlate with protection from cardiovascular events and renal disease in patients with SLE. *Clin Immunol* 142, 390-398 (2012).
47. Deane, R. et al. RAGE mediates amyloid-beta peptide transport across the blood-brain barrier and accumulation in brain. *Nat Med* 9, 907-913 (2003).
48. Leclerc, E., Fritz, G., Vetter, S. W. & Heizmann, C. W. Binding of S100 proteins to RAGE: an update. *Biochim Biophys Acta* 1793, 993-1007 (2009).
49. Wang, H. et al. HMG-1 as a late mediator of endotoxin lethality in mice. *Science* 285, 248-251 (1999).
50. Hur, E. M. et al. LIME, a novel transmembrane adaptor protein, associates with p56lck and mediates T cell activation. *J Exp Med* 198, 1463-1473 (2003).
51. Roederer, M. Interpretation of cellular proliferation data: avoid the panglossian. *Cytometry. Part A: the journal of the International Society for Analytical Cytology* 79, 95-101 (2011).

What is claimed is:

1. A polypeptide comprising (A) a C1q dodecamer peptide wherein the dodecamer peptide comprises KGEQGEPGAPGI (SEQ ID NO:3) or a C1q nonamer peptide wherein the nonamer peptide comprises KGEQGEPGA (SEQ ID NO:5), linked to (B) (i) a High Mobility Group Box 1 (HMGB1) A-box peptide, or (ii) a HMGB1 B-box peptide, or (iii) a DWEYS peptide, and wherein when the fusion protein comprises the HMGB1 A-box peptide it has SEQ ID NO:10, and wherein when the fusion protein comprises the DWEYS peptide it has SEQ ID NO:11.

2. The polypeptide of claim 1, wherein the carboxy terminal amino acid or the amino terminal amino acid residue of the C1q dodecamer or nonamer is bound to the amino terminal amino acid or the carboxy terminal amino acid residue, respectively, of the HMGB1 A-box or HMGB1 B-box peptide.

3. The polypeptide of claim 1, wherein the C1q dodecamer or nonamer is bound directly by a peptide bond to the HMGB1 A-box or HMGB1 B-box peptide.

4. The polypeptide of claim 1, wherein the C1q dodecamer or nonamer is bound by a peptide bond to a linker peptide which is bound by a peptide bond to the HMGB1 A-box or HMGB1 B-box peptide.

5. A method of treating an autoimmune inflammatory condition in a subject comprising administering an amount of the polypeptide or composition of claim 1 effective to treat an autoimmune inflammatory condition.

6. The method of claim 5, wherein the autoimmune inflammatory condition is systemic lupus erythematosus (SLE).

7. A method to quiesce a monocyte in a subject comprising administering an amount of the polypeptide of claim 1 effective to quiesce a monocyte in a subject.

* * * * *